(12) United States Patent
Ogawa et al.

(10) Patent No.: US 11,278,675 B2
(45) Date of Patent: Mar. 22, 2022

(54) PLUNGER ASSEMBLY, DRUG SOLUTION DOSAGE DEVICE, AND DRIVING METHOD OF PLUNGER ASSEMBLY

(71) Applicant: TERUMO KABUSHIKI KAISHA, Tokyo (JP)

(72) Inventors: Junichi Ogawa, Yamanashi (JP); Akira Kondo, Kanagawa (JP); Ruriko Iibuchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 58 days.

(21) Appl. No.: 16/819,788

(22) Filed: Mar. 16, 2020

(65) Prior Publication Data

US 2020/0215270 A1    Jul. 9, 2020

Related U.S. Application Data

(63) Continuation of application No. PCT/JP2018/036197, filed on Sep. 28, 2018.

(30) Foreign Application Priority Data

Sep. 29, 2017    (JP) .............. JP2017-190198

(51) Int. Cl.
  *A61M 5/315*    (2006.01)
  *A61M 5/145*    (2006.01)
(52) U.S. Cl.
  CPC ........ *A61M 5/31511* (2013.01); *A61M 5/145* (2013.01); *A61M 5/1452* (2013.01);
  (Continued)

(58) Field of Classification Search
  CPC ............... A61M 5/145; A61M 5/1452; A61M 5/14546; A61M 5/1456; A61M 5/14566;
  (Continued)

(56) References Cited

U.S. PATENT DOCUMENTS

2006/0184154 A1    8/2006    Moberg et al.
2009/0326459 A1    12/2009    Shipway et al.
(Continued)

FOREIGN PATENT DOCUMENTS

JP    2014057886 A    4/2014
JP    2015181869 A    10/2015
(Continued)

OTHER PUBLICATIONS

International Search Report (PCT/ISA/210) dated Nov. 13, 2018, by the Japan Patent Office as the International Searching Authority for International Application No. PCT/JP2018/036197.
(Continued)

*Primary Examiner* — Shefali D Patel
(74) *Attorney, Agent, or Firm* — Buchanan Ingersoll & Rooney PC

(57) ABSTRACT

A plunger assembly of a drug solution dosage device includes a feed screw including a male thread portion and an extending portion, a first plunger including a first female thread portion, a second plunger including a nut accommodating portion, a nut member including a second female thread portion, and a base portion that guides the second plunger. The nut accommodating portion accommodates the nut member so that the nut member is non-rotatable and movable in an axial direction.

22 Claims, 31 Drawing Sheets

(52) U.S. Cl.
CPC ........ *A61M 5/315* (2013.01); *A61M 5/31528* (2013.01); *A61M 5/31583* (2013.01); *A61M 5/14566* (2013.01); *A61M 2005/3152* (2013.01)

(58) Field of Classification Search
CPC .............. A61M 5/315; A61M 5/31511; A61M 5/31515; A61M 5/31528; A61M 5/31583; A61M 2005/14506; A61M 2005/14573; A61M 2005/31518; A61M 2005/3152
See application file for complete search history.

(56) References Cited

U.S. PATENT DOCUMENTS

| | | |
|---|---|---|
| 2015/0032084 A1 | 1/2015 | Cabiri |
| 2015/0297827 A1 | 10/2015 | Hanson et al. |
| 2017/0175859 A1 | 6/2017 | Brockmeier |

FOREIGN PATENT DOCUMENTS

| | | |
|---|---|---|
| JP | 2015530153 A | 10/2015 |
| WO | 2013148270 A2 | 10/2013 |

OTHER PUBLICATIONS

Written Opinion (PCT/ISA/237) dated Nov. 13, 2018 dated Oct. 2, 2018, by the Japan Patent Office as the International Searching Authority for International Application No. PCT/JP2018/036197 PCT/JP2018/027217.

The extended European Search Report dated Jun. 29, 2020, by the European Patent Office in corresponding European Patent Application No. 18860131.4-1122. (9 pages).

An English Translation of the International Search Report (Form PCT/ISA/210) and the Written Opinion of the International Searching Authority (Form PCT/ISA/237) dated Nov. 13, 2018, by the Japanese Patent Office in corresponding International Application No. PCT/JP2018/036197. (6 pages).

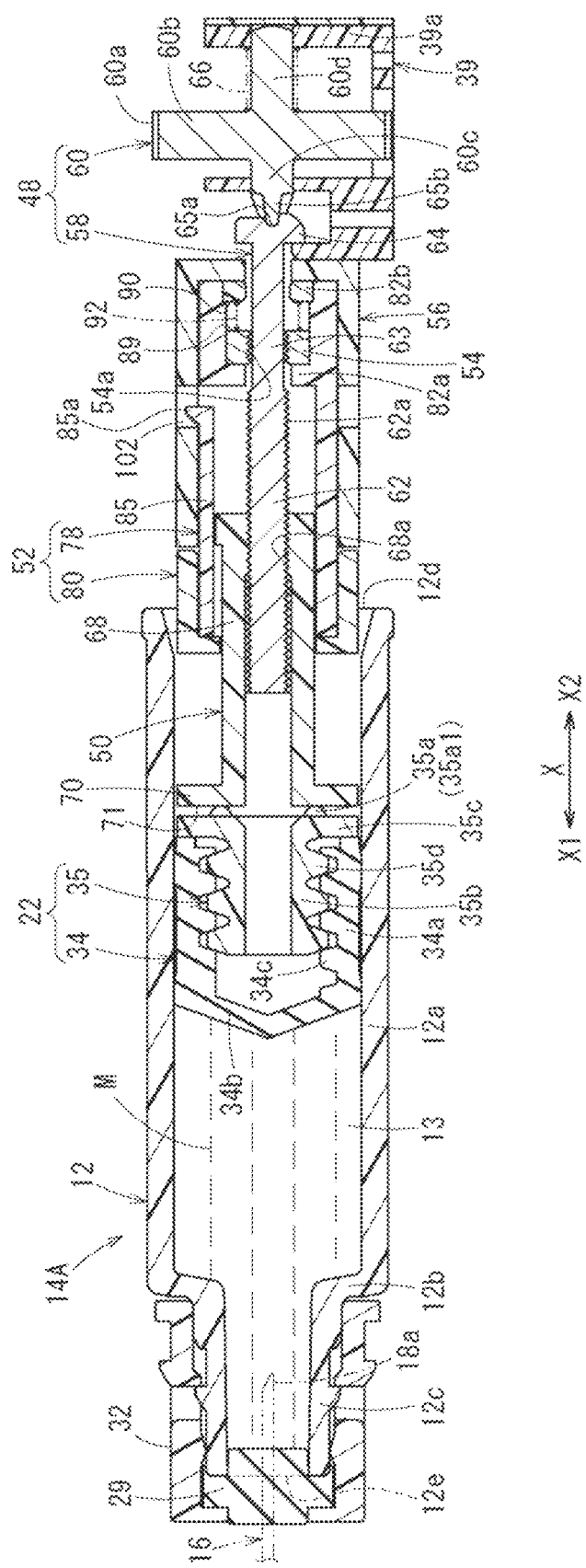

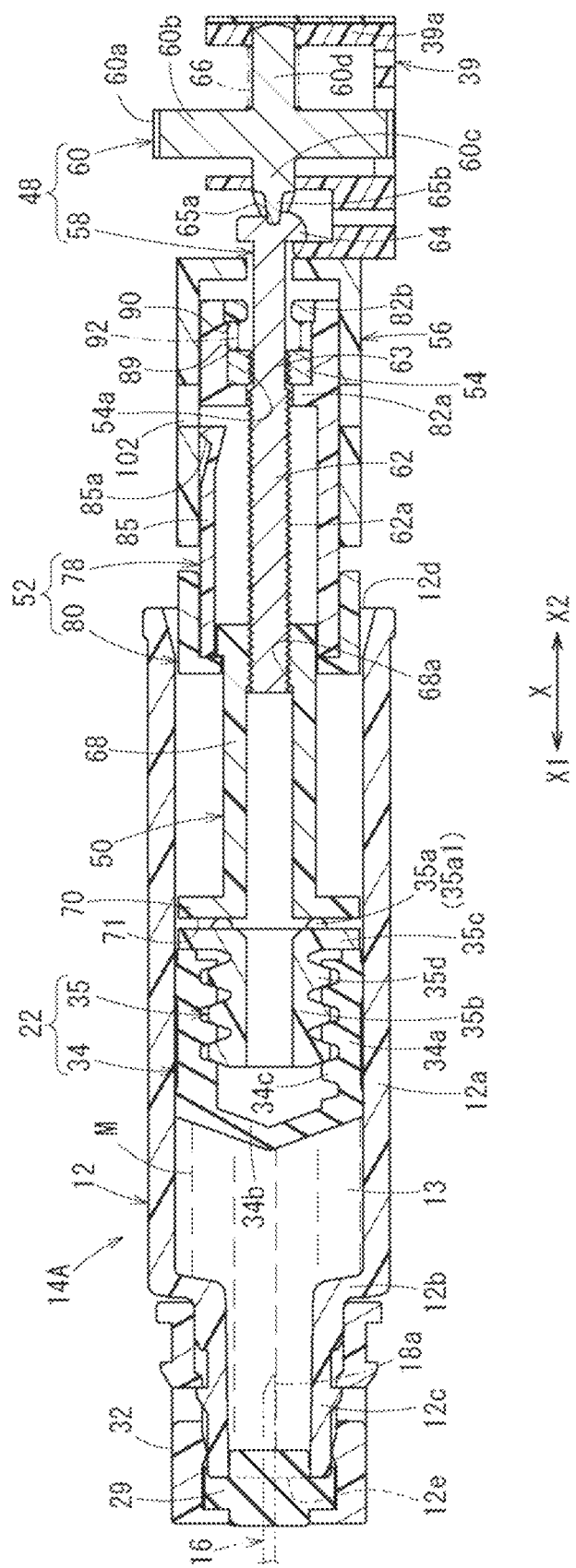

PLUNGER ASSEMBLY, DRUG SOLUTION DOSAGE DEVICE, AND DRIVING METHOD OF PLUNGER ASSEMBLY

CROSS-REFERENCES TO RELATED APPLICATIONS

This application is a continuation of International Application No. PCT/JP2018/036197 filed on Sep. 28, 2018, which claims priority to Japanese Application No. 2017-190198 filed on Sep. 29, 2017, the entire content of both of which is incorporated herein by reference.

FIELD OF THE DISCLOSURE

The present disclosure generally relates to a plunger assembly, a drug solution dosage device, and a driving method of the plunger assembly.

BACKGROUND DISCUSSION

Syringe pump type drug solution dosage devices administer a drug solution filled in a cylinder into a living body under the pressing action of a plunger are known. Further, for example, as disclosed in International Patent Application Publication No. 2013/148270 A, in this type of drug solution dosage device, a mechanism that causes a plunger and a screw shaft to be threadedly engaged with each other, and the plunger is caused to move forward under the rotating action of the screw shaft is known.

In recent years, drug solution dosage devices have been downsized, and a type that is applied to a body has appeared. In particular, in the case of a drug solution dosage device of the type that is applied to a body, the size of the drug solution dosage device has been reduced as much as possible from the viewpoint of the limited area that can be applied and usability. The effect of reducing the size of the drug solution dosage device is not sufficient because only a single plunger moves forward with respect to the screw shaft.

SUMMARY

A plunger assembly, a drug solution dosage device, and a method of driving the plunger assembly are disclosed, which can effectively downsize the device.

A plunger assembly is disclosed that is extendable in an axial direction, and with the extension, presses a gasket slidably arranged inside a drug solution container to feed or delivery (i.e., push out) a drug solution from the drug solution container, the plunger assembly including: a feed screw including a rod portion, the rod portion including a male thread portion having a male thread formed thereon, and an extending portion extending from a proximal end of the male thread portion in a proximal direction and not having the male thread formed thereon; a first plunger including a gasket pressing portion that is capable of pressing the gasket, a first female thread portion threadedly engaged with the male thread portion of the feed screw at least in an initial state before the plunger assembly starts an extension operation, and a first guided portion, a first engagement portion, and a first abutment portion; a second plunger including a first guide portion, a second guided portion, a second engagement portion, a second abutment portion, and a nut accommodating portion; a nut member having a second female thread portion formed on an inner periphery of the nut member, and into which the feed screw is inserted; and a base portion on which a second guide portion is formed, in which the first guide portion of the second plunger is engaged with the first guided portion of the first plunger, prevents rotation of the first plunger with respect to the second plunger, and guides movement of the first plunger in the axial direction, in which the second guide portion of the base portion is engaged with the second guided portion, prevents rotation of the second plunger with respect to the base portion, and guides movement of the second plunger in the axial direction, in which the nut accommodating portion accommodates the nut member so that the nut member is non-rotatable and movable in the axial direction, in which the extending portion of the feed screw is inserted into the nut member in the initial state, in which, when the first plunger moves forward by a predetermined length with rotation of the feed screw, the first engagement portion of the first plunger comes into abutment against the second engagement portion of the second plunger, and the first plunger causes the second plunger to move forward, in which, with the forward movement of the second plunger, the nut member moves forward, and the second female thread portion is threadedly engaged with the male thread portion of the feed screw, and in which, after the thread engagement between the second female thread portion and the male thread portion is started, the second abutment portion of the second plunger comes into abutment against the first abutment portion of the first plunger, and the second plunger moving forward causes the first plunger to move forward.

The plunger assembly configured as described above extends in a plurality of stages, so that the overall length can be shortened, and accordingly, the drug solution dosage device to which the plunger assembly is mounted can be downsized. The downsizing of the device makes it possible to reduce the area required for application when the device is applied to a patient's body surface, so that the device can be rather easily applied to applications such as application to the patient's body surface. In addition, the downsizing of the device can help improve usability such as carrying and storing. In addition, since the nut member is movable in the axial direction relative to the second plunger, even when the male thread portion of the feed screw and the second female thread portion of the nut member do not mesh with each other at the same time as the contact between the male thread portion of the feed screw and the nut member, these can be threadedly engaged with each other when the phase of the male thread portion and the phase of the second female thread portion match with each other thereafter. Therefore, the second plunger can be reliably caused to move forward through the nut member by the feed screw.

The plunger assembly may further include a nut urging member that urges the nut member in a distal direction, the nut accommodating portion of the second plunger may include a distal-end pedestal portion and a proximal-end pedestal portion, and, in the initial state, a distal end surface of the nut member may be held in abutment against the distal-end pedestal portion, a distal end of the nut urging member may be held in abutment against a proximal end surface of the nut member, and a proximal end of the nut urging member may be held in abutment against the proximal-end pedestal portion.

In accordance with an aspect, since the nut member is always urged in the distal direction, when the phase of the male thread portion of the feed screw and the phase of the second female thread portion of the nut member match with each other, the feed screw and the nut member can be reliably threadedly engaged with each other. That is, while the second plunger moves forward by the pitch of the male thread portion, the feed screw and the nut member are always threadedly engaged with each other.

A plurality of ribs extending along the axial direction and arranged at intervals in a circumferential direction may be formed on an inner peripheral surface of the nut accommodating portion, and the plurality of ribs may be held in abutment against an outer peripheral surface of the nut member.

With the above-mentioned configuration, the sliding resistance of the nut member with respect to the second plunger can be reduced, and the relative axial movement of the nut member with respect to the second plunger can be made rather smooth.

A distal end of the first plunger may include a flange portion that is capable of being held in abutment against an inner peripheral surface of the drug solution container, and with this configuration, buckling of the first plunger can be prevented.

The second plunger may include a plunger main-body portion including the nut accommodating portion, the first guide portion, the second guided portion, and the second abutment portion; and a cap member fixed to the plunger main-body portion and including the second engagement portion.

In accordance with an aspect, the second plunger including the first guide portion, the second guided portion, the second abutment portion, and the second engagement portion can be rather easily manufactured by injection molding.

The cap member may include a distal-end outer peripheral portion that is capable of being held in abutment against an inner peripheral surface of the drug solution container, such that buckling of the second plunger can be prevented.

The first guide portion of the second plunger may include an axial guide that extends along the axial direction and guides the first guided portion of the first plunger in the axial direction, and a rotation guide that is continuous with a distal end of the axial guide and extends in a circumferential direction to guide the first guided portion in the circumferential direction.

With the above-mentioned configuration, the first plunger can be rotated with the rotation of the feed screw at the distal end of the first guide portion.

The rotation guide may include a first end portion continuous with the axial guide, and a second end portion different from the first end portion, the first guide portion of the second plunger may include a lock portion that is continuous with the second end portion of the rotation guide, and the lock portion may extend from the second end portion in the proximal direction with a length shorter than the axial guide, and be capable of locking the first guided portion of the first plunger.

With the above-mentioned configuration, the first guided portion is prevented from returning to the axial guide of the first guide portion.

The second plunger may include a temporary locking elastic piece including a temporary locking claw portion provided at an end portion of the temporary locking elastic piece, and the base portion may include a temporary locking concave portion into which the temporary locking claw portion is disengageably inserted.

In accordance with an aspect, since the second plunger is temporarily fixed to the base portion, the second plunger can be prevented from moving forward by following the forward movement of the first plunger before the feed screw is threadedly engaged with the nut member.

The first plunger may include a support protrusion that supports the temporary locking claw portion from inside.

With the above-mentioned configuration, the temporary locking claw portion can be prevented from being disengaged from the temporary locking concave portion until the first plunger moves forward to some extent.

Further, a drug solution dosage device of the present disclosure includes the plunger assembly described above; a drive mechanism that rotates the feed screw; the drug solution container including a body portion filled with the drug solution; the gasket; and a casing that accommodates the drug solution container.

According to the drug solution dosage device configured as described above, downsizing of the drug solution dosage device can be achieved and the second plunger can be reliably caused to move forward by the feed screw.

The drive mechanism may include a motor and a drive gear attached to the motor, and the feed screw may include a driven gear coupled to the rod portion and driven by the drive gear.

Thus, the feed screw can be rotated with a rather simple configuration.

The casing may include a first opening into which the drug solution container is inserted, the drug solution container may have a distal end portion protruding from the casing through the first opening, and a ring-shaped waterproof packing may be arranged between the vicinity of the distal end portion of the drug solution container and the casing.

With the above-mentioned configuration, water can be prevented from entering the casing through the first opening.

The casing may include a casing main-body portion including an accommodating portion that accommodates the drug solution container and a second opening provided in the accommodating portion; a lid that seals the second opening, and an annular waterproof member attached to a rim of the second opening and in close contact with the lid.

With the above-mentioned configuration, water can be prevented from entering the casing through the second opening.

The drug solution dosage device may further include a chassis structure in which the drug solution container, the drive mechanism, and the plunger assembly are fixed at predetermined positions, respectively, the chassis structure may be arranged in the casing, and the second opening may be formed to be larger than the chassis structure.

With the above-mentioned configuration, the plunger assembly can be rather easily taken out of the casing together with the chassis structure through the second opening.

The first plunger may be capable of rotating by a predetermined angle with respect to the second plunger with rotation of the feed screw at a distal end of the first guide portion of the second plunger, the gasket may include: a gasket main body made of a first material having elasticity; and an abutment member made of a second material harder than the first material and mounted to a proximal end of the gasket main body, the abutment member may include a pressed portion pressed by the gasket pressing portion, and the gasket pressing portion may be made of a material harder than the first material.

With the above-mentioned configuration, the sliding resistance of the first plunger in the rotation direction with respect to the gasket can be reduced. Therefore, the gasket does not hinder the rotation of the first plunger.

The abutment member may include an insertion portion inserted into the gasket main body, and a proximal-end flange portion provided at a proximal end of the insertion portion, the proximal-end flange portion may include the pressed portion on a proximal end surface of the proximal-end flange portion, and the pressed portion may be a plurality of convex portions provided intermittently on the proximal end surface and protruding from the proximal end surface in the proximal direction.

With the above-mentioned configuration, the sliding resistance of the first plunger in the rotation direction with respect to the gasket can be effectively reduced.

Each of the plurality convex portions may have a dome shape that bulges toward the proximal end With this configuration, the sliding resistance of the first plunger in the rotation direction with respect to the gasket can be more effectively reduced.

Further, according to the present disclosure, a driving method is disclosed of the plunger assembly described above, in which, with rotation of the feed screw, the first plunger moves forward along the axial direction, in which the first engagement portion of the first plunger is engaged with the second engagement portion of the second plunger, and the first plunger moving forward causes the second plunger to move forward, in which, with the forward movement of the second plunger, the nut member moves in the proximal direction relative to the second plunger, and the movement of the nut member causes the nut member to be threadedly engaged with the male thread portion of the feed screw, and in which the nut member threadedly engaged with the male thread portion moves forward with rotation of the feed screw to cause the second plunger to move forward, and the second plunger moving forward causes the first plunger to move forward.

Thereby, the male thread portion of the feed screw and the second female thread portion of the nut member can be threadedly engaged with each other rather smoothly. Therefore, the second plunger can be reliably caused to move forward through the nut member by the feed screw.

In the driving method of the plunger assembly described above, the nut member may be urged in a distal direction by a nut urging member, and, after the nut member moves in the proximal direction relative to the second plunger against an urging force of the nut urging member, the second female thread portion of the nut member may be threadedly engaged with the male thread portion of the feed screw.

Thereby, the feed screw and the nut member can be reliably threadedly engaged with each other.

In the driving method of the plunger assembly described above, the first plunger restricted in rotation with respect to the feed screw may move to the vicinity of the distal end of the second plunger, the first plunger that has moved to the vicinity of the distal end of the second plunger may rotate by a predetermined angle in accordance with rotation of the feed screw, the first plunger that has rotated by the predetermined angle may be restricted in rotation again, and the first engagement portion of the first plunger may be engaged with the second engagement portion of the second plunger, and the first plunger in which the first engagement portion is engaged with the second engagement portion may move forward while pulling the second plunger.

Accordingly, the second plunger can be caused to move forward by the first plunger moving forward with the rotation of the feed screw.

In the driving method of the plunger assembly described above, in a state where the male thread portion of the feed screw is threadedly engaged with both the first female thread portion and the second female thread portion, the feed screw may rotate, and the first plunger and the second plunger may move forward, after the second plunger moves forward by a predetermined length, the first female thread portion of the first plunger may be disengaged from the male thread portion, and the second plunger may cause the first plunger to move forward in a state where the first female thread portion is disengaged from the male thread portion and the second female thread portion is threadedly engaged with the male thread portion.

Thereby, the transition from the double screw state in which the male thread portion of the feed screw is threadedly engaged with both the first female thread portion and the second female thread portion to the state in which only the second female thread portion and the male thread portion are threadedly engaged with each other is performed rather smoothly, and the first plunger can be caused to move forward by the second plunger.

According to the plunger assembly, the drug solution dosage device, and the driving method of the plunger assembly of the present disclosure, the device can be downsized.

BRIEF DESCRIPTION OF THE DRAWINGS

FIG. 11 is a first view illustrating an operation of the plunger assembly.

FIG. 14 is a fifth view illustrating the operation of the plunger assembly.

DETAILED DESCRIPTION

Set forth below with reference to the accompanying drawings is a detailed description of embodiments of a plunger assembly, a drug solution dosage device, and a driving method of the plunger assembly representing examples of the inventive plunger assembly, the drug solution dosage device, and the driving method of the plunger assembly.

Figure 1:
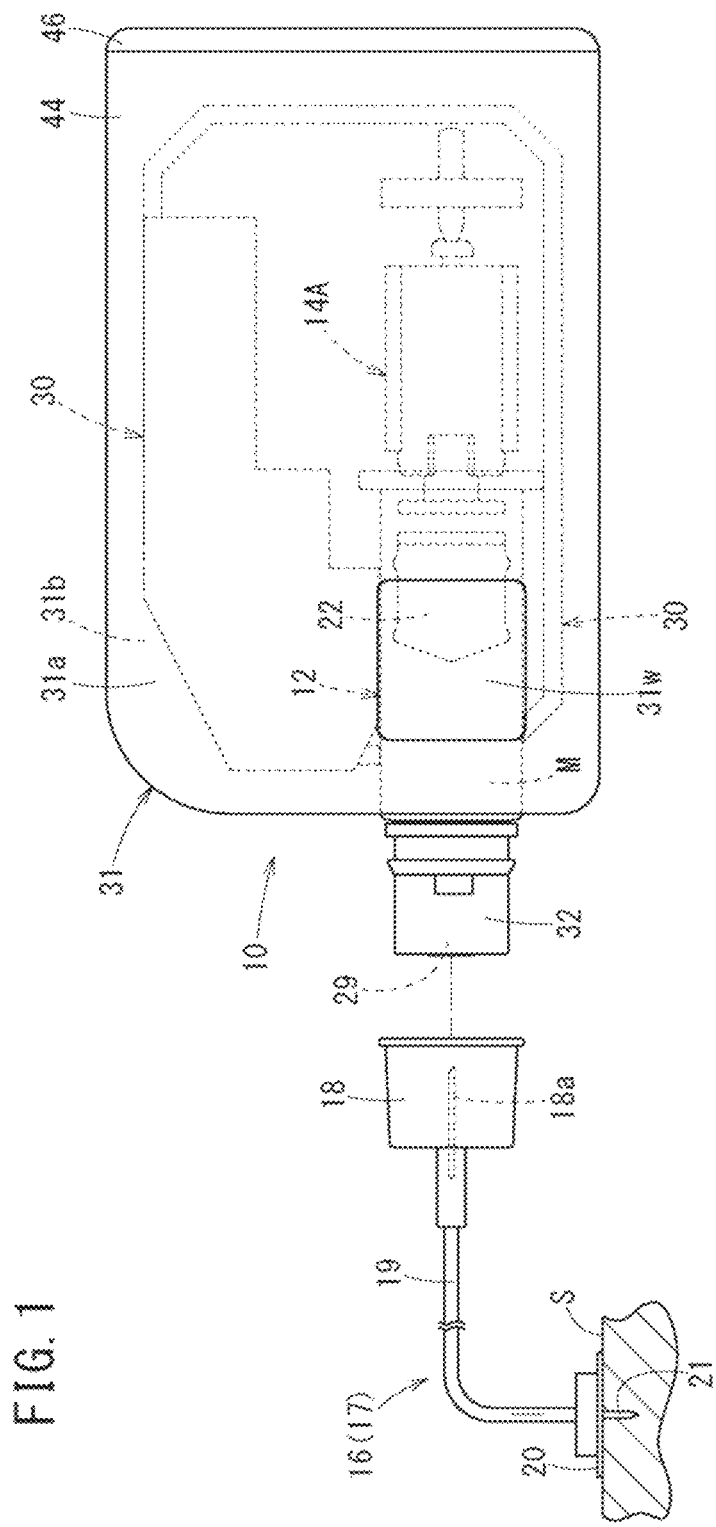
FIG. 1 is a schematic plan view of a drug solution dosage device according to an embodiment.

A drug solution dosage device 10 according to the present embodiment illustrated in FIG. 1 is used to administer a drug solution M into a living body. The drug solution dosage device 10 continuously administers the drug solution M filled in a drug solution container 12 into a living body over a relatively long time (for example, about several minutes to several hours) under the pressing action of a plunger assembly 14A. The drug solution dosage device 10 may intermittently administer the drug solution M into a living body. Examples of the drug solution M include protein preparations, narcotic analgesics, and diuretics.

As illustrated in FIG. 1, at the time of using the drug solution dosage device 10, as an administration device (i.e., dosage device) 16, for example, a patch-type tubular needle 17 is connected to the drug solution administration device 10, and the drug solution M discharged from the drug solution container 12 is injected into a patient's body through the tubular needle 17. The tubular needle 17 includes a connector 18 connectable to a distal end portion 12c of the drug solution container 12, a flexible liquid feeding tube 19 having one end connected to the connector 18, a patch portion 20 which is connected to the other end of the liquid feeding tube 19 and is capable of being stuck to a skin S, and a puncture needle 21 protruding from patch portion 20. The puncture needle 21 is punctured substantially perpendicularly to the skin S. Note that the puncture needle 21 may be punctured obliquely to the skin S.

Note that the dosage device 16 connected to the drug solution dosage device 10 is not limited to the patch-type tubular needle 17 described above, and may be, for example, one in which a puncture needle (wing-like needle or the like) is connected to the distal end of the liquid feeding tube 19. Alternatively, the dosage device 16 may be a bent needle which is connectable to the distal end portion 12c of the drug solution container 12 without intermediation of the liquid feeding tube 19. In this case, the bent needle is bent downward at, for example, about 90° (i.e., 90 degrees) from the distal end portion 12c of the drug solution container 12, and is punctured perpendicularly to the skin S with the fixing (applying) of the drug solution dosage device 10 to the skin S. Further, the distal end portion 12c of the drug solution container 12, the dosage device 16, and a part of the needle may be inside the drug solution container 12, and the tip of the needle may protrude from the drug solution container 12. Also in this case, the needle is punctured perpendicularly to the skin S with fixing (applying) of the drug solution dosage device 10 to the skin S.

Figure 2:
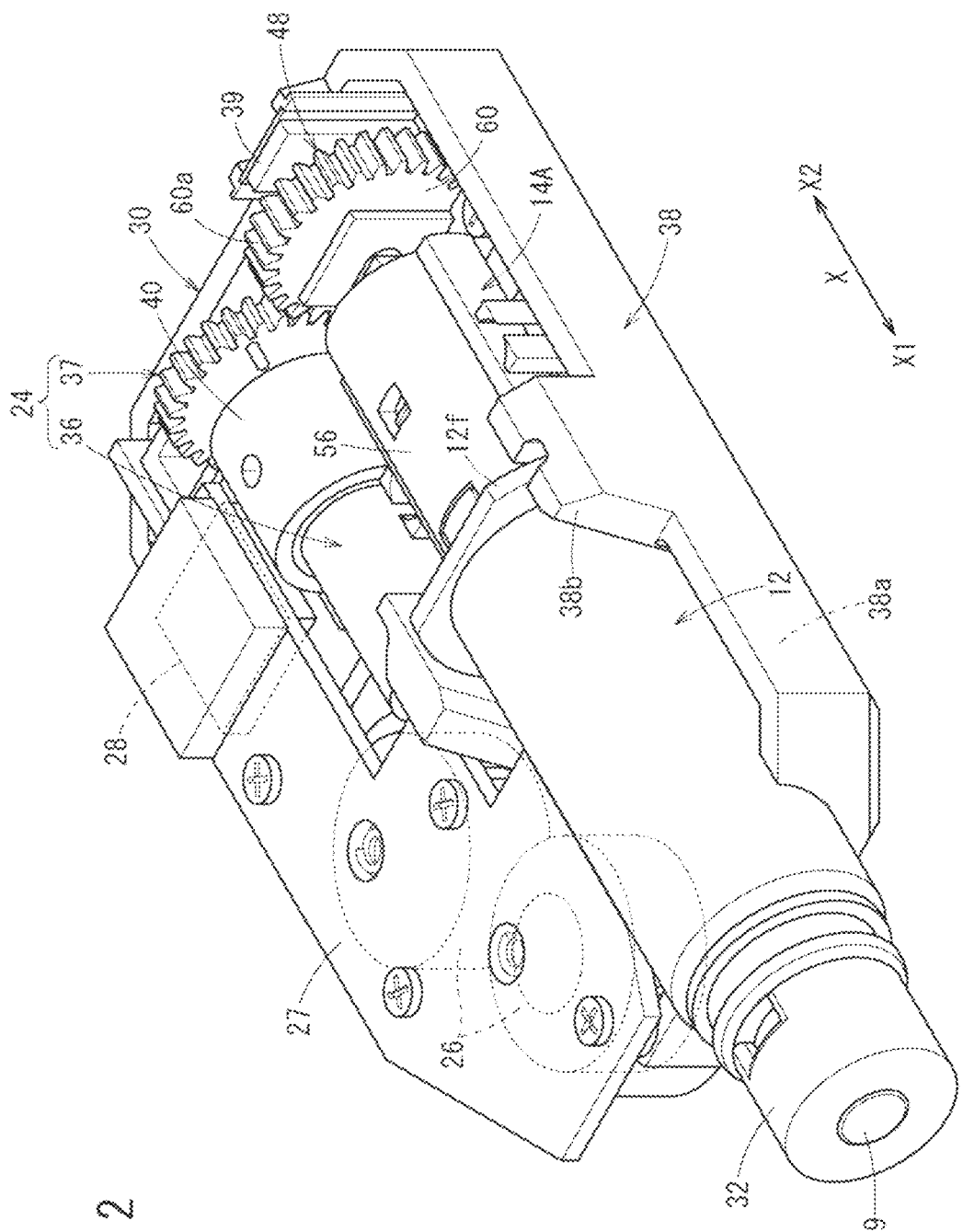
FIG. 2 is a perspective view of an internal mechanism of the drug solution dosage device.

As illustrated in FIG. 1 or FIG. 2, the drug solution dosage device 10 includes the drug solution container 12 filled with the drug solution M, a gasket 22 slidably arranged in the drug solution container 12, a plunger assembly 14A that is extendable in an axial direction (direction of the arrow X) and is capable of pressing the gasket 22 in the distal direction (direction of the arrow X1), a drive mechanism 24 that drives the plunger assembly 14A, batteries 26 that supply electric power necessary for an operation of the drug solution dosage device 10, a control unit 28 that controls the drive mechanism 24, a chassis structure 30 that supports the drug solution container 12, the plunger assembly 14A, and the drive mechanism 24, and a casing 31 that accommodates these components.

Figure 3:
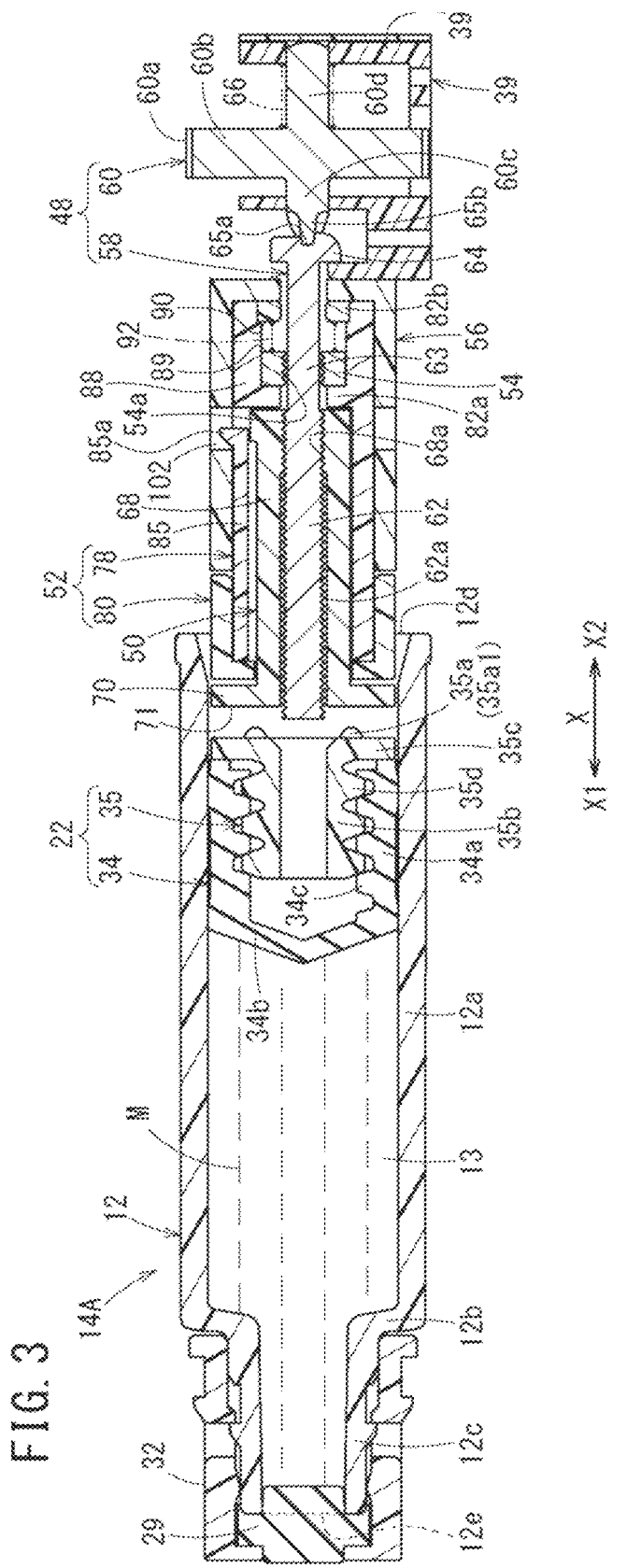
FIG. 3 is a cross-sectional view of a plunger assembly according to the embodiment taken along an axial direction.

As illustrated in FIGS. 2 and 3, the drug solution container 12 has a generally hollow cylindrical shape having a drug solution chamber 13 in the drug solution container 12. Specifically, the drug solution container 12 includes a body portion 12a having a constant inner diameter and outer diameter in the axial direction, a shoulder portion 12b reduced in diameter from the distal end of the body portion 12a, and the distal end portion 12c protruding from the shoulder portion 12b in the distal direction. A proximal-end opening 12d is formed at the proximal end of the body portion 12a. A discharge port 12e communicating with the drug solution chamber 13 is formed at the distal end portion 12c. The drug solution M is filled in the drug solution container 12 in advance. The drug solution container 12 is preferably fabricated from a transparent material.

In FIG. 3, the discharge port 12e is sealed by a sealing member 29 fabricated from an elastic resin material such as a rubber material or an elastomer material in a liquid-tight manner. When the connector 18 illustrated in FIG. 1 is connected to the distal end portion 12c, the sealing member 29 is punctured by a needle 18a provided on the connector 18. The sealing member 29 is fixed to the distal end portion 12c of the drug solution container 12 by a fixing cap 32 having an opening at the distal end. The distal end surface of the sealing member 29 is exposed from the opening of the fixing cap 32.

The gasket 22 closes the proximal end side of the drug solution chamber 13 in a liquid-tight manner. In the initial state of the drug solution dosage device 10, the gasket 22 is located on the distal end side with respect to the proximal end of the drug solution container 12. The gasket 22 includes a gasket main body 34 and an abutment member 35 mounted to a proximal end of the gasket main body 34. The gasket main body 34 is made of a first material having elasticity. Examples of the first material can be an elastic resin material such as a rubber material or an elastomer material.

The outer peripheral portion of the gasket main body 34 is in contact with the inner peripheral surface of the drug solution container 12 (body portion 12a) in a liquid-tight manner. The gasket main body 34 includes a base portion 34a whose outer peripheral surface is in contact with the body portion 12a of the drug solution container 12 in a liquid-tight manner, and a conical portion 34b that protrudes from the base portion 34a in the distal direction and is reduced in diameter so as to be tapered in the distal direction.

The abutment member 35 is made of a second material harder than the first material. The abutment member 35 includes a pressed portion 35a pressed by a gasket pressing portion 71 described later of the plunger assembly 14A. Further, the abutment member 35 includes an insertion portion 35b inserted into the gasket main body 34, and a proximal-end flange portion 35c provided at the proximal end of the insertion portion 35b.

A male thread 35d provided on an outer peripheral portion of the insertion portion 35b is threadedly engaged with a female thread 34c provided on an inner peripheral portion of the gasket main body 34. The proximal-end flange portion 35c includes the pressed portion 35a on the proximal end surface. The pressed portion 35a can be a plurality of convex portions 35a1 provided intermittently on the proximal end surface of the proximal-end flange portion 35c and protruding from the proximal end surface in the proximal direction (direction of the arrow X2). The convex portions 35a1 have a dome shape that bulges toward the proximal end.

The plunger assembly 14A is configured to be extendable in the axial direction under the driving action of the drive mechanism 24, to cause the gasket 22 to move forward (i.e., distal direction) in the drug solution container 12 with the extension, and to feed or delivery (i.e., push out) the drug solution M from the drug solution container 12. In the initial state of the drug solution dosage device 10, the distal end side of the plunger assembly 14A is inserted into the proximal end side of the drug solution container 12. The details of the plunger assembly 14A will be described later.

In FIG. 2, the drive mechanism 24 includes a motor 36 that is driven and controlled under the control of the control unit 28 using the batteries 26 as a power source, and a drive gear 37 fixed to an output shaft of the motor 36.

As illustrated in FIG. 1, the chassis structure 30 is arranged in the casing 31. As illustrated in FIG. 2, the drug solution container 12, the drive mechanism 24, and the plunger assembly 14A are fixed to predetermined positions of the chassis structure 30, respectively. The chassis structure 30 includes a chassis main-body member 38, a support member 39 that is fixed to the chassis main-body member 38 and rotatably supports a feed screw 48 of the plunger assembly 14A, and a motor holding member 40 that is fixed to the chassis main-body member 38 and holds the motor 36 between the chassis structure 30 and the chassis main-body member 38.

The chassis main-body member 38 includes a base plate portion 38a (see also FIG. 10A) constituting a bottom wall portion, and a flange mounting portion 38b that protrudes from the upper surface of the base plate portion 38a in the thickness direction (upward) of the base plate portion 38a and to which a flange portion 12f of the drug solution container 12 is mounted. An electric board 27 to which the control unit 28 and the batteries 26 are attached is fixed to the chassis main-body member 38.

In FIG. 1, the casing 31 is a hollow member configured to accommodate the drug solution container 12, the gasket 22, the plunger assembly 14A, the drive mechanism 24, the batteries 26, the control unit 28, and the chassis structure 30 which are described above. The distal end portion 12c of the drug solution container 12 protrudes from the casing 31 and is exposed to the outside of casing 31. The casing 31 includes an upper surface 31a and a bottom surface 31b. A window portion 31w fabricated from a transparent material is provided on the upper surface 31a of the casing 31, and the amount of liquid remaining in the drug solution container 12 can be checked through the window portion 31w.

The drug solution dosage device 10 may be configured as a patch type that is applied to the skin S of a patient, for example. In the case of such a patch type, a sheet-shaped sticking portion (adhesive portion) that is capable of being stuck to the skin S is provided on the bottom surface 31b of the casing 31. In the initial state of the drug solution dosage device 10, a peelable protection sheet is applied to the sticking surface of the sticking portion.

Note that the drug solution dosage device 10 may be configured as a type in which a mounting tool such as a hook or a clip is provided on the bottom surface 31b of the casing 31, and it is attached to patient's clothes (for example, a waist portion of pants) by hooking it.

Figure 4:
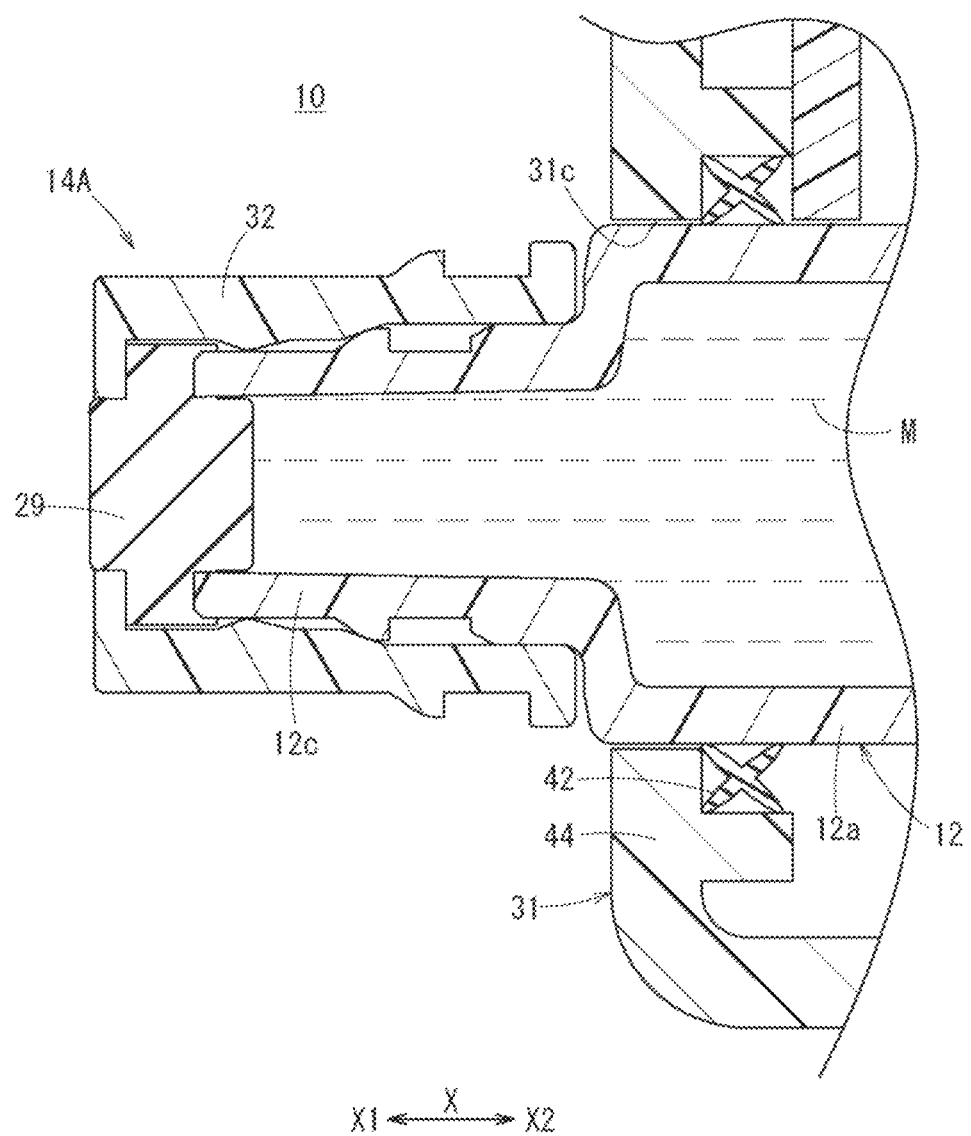
FIG. 4 is a cross-sectional view around a first opening of a casing of the drug solution dosage device illustrated in FIG. 1.

As illustrated in FIG. 4, the casing 31 has a first opening 31c into which the drug solution container 12 is inserted. The distal end portion of the drug solution container 12 protrudes from the casing 31 through the first opening 31c. A ring-shaped waterproof packing (i.e., an O-ring) 42 is arranged between the vicinity of the distal end portion of the drug solution container 12 and the casing 31. The waterproof packing 42 has an X-shaped cross-sectional shape, and is arranged in the first opening 31c. The outer peripheral portion of the waterproof packing 42 is in close contact with the inner surface of the first opening 31c over the entire circumference in a liquid-tight manner, and the inner peripheral portion of the waterproof packing 42 is in contact with the outer peripheral surface of the drug solution container 12 (body portion 12a) over the entire circumference in a liquid-tight manner. Note that the waterproof packing 42 may have an O-shaped cross-sectional shape.

Figure 5:
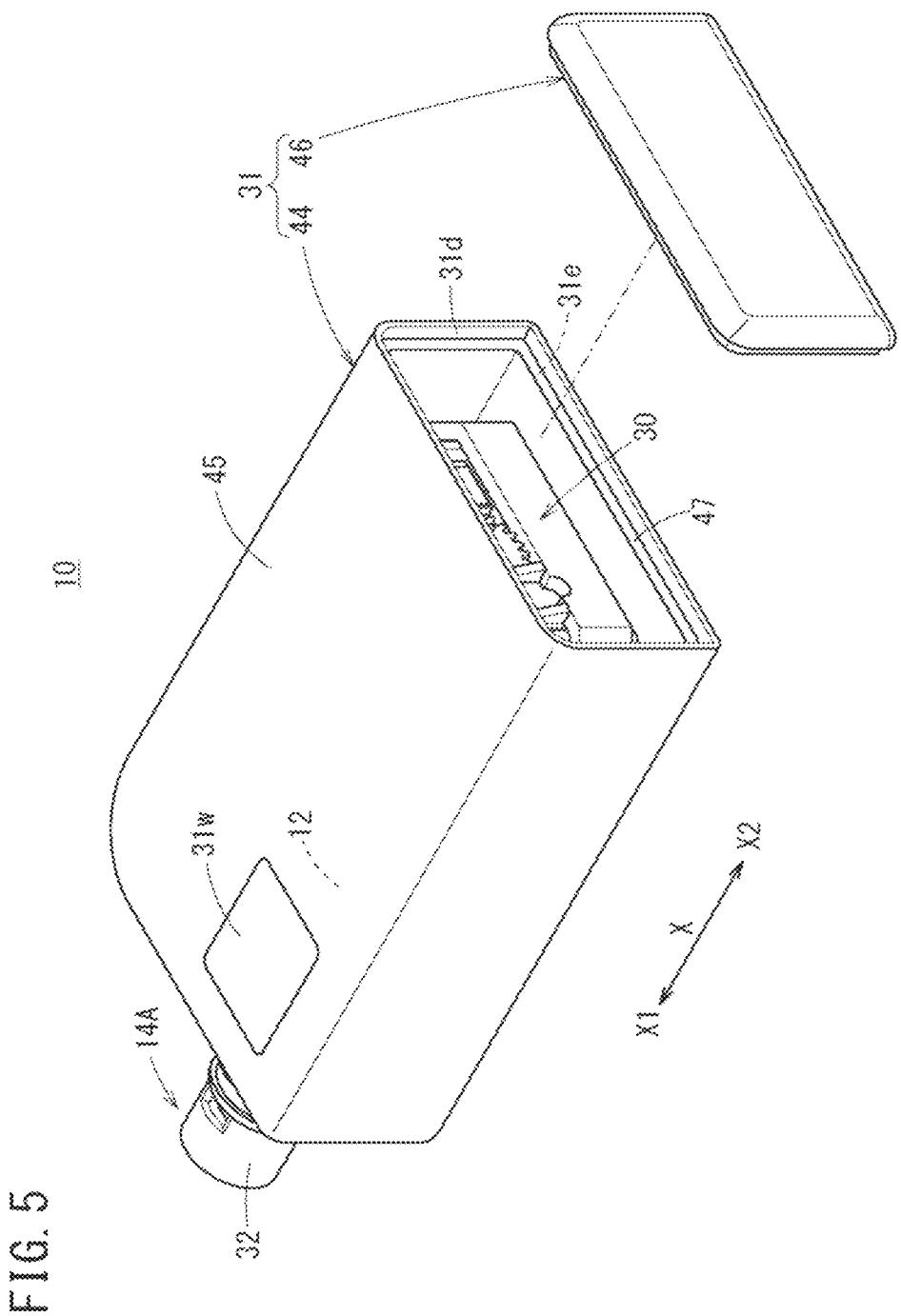
FIG. 5 is a perspective view illustrating a structure of the casing of the drug solution dosage device illustrated in FIG. 1.

As illustrated in FIG. 5, the casing 31 includes a casing main-body portion 44 including an accommodating portion 45 that accommodates the drug solution container 12 and a second opening 31d provided in the accommodating portion 45, a lid 46 that seals the second opening 31d, and an annular waterproof member 47 attached to the rim of the second opening 31d and in contact with the lid 46. The first opening 31c (FIG. 4) described above is provided in the casing main-body portion 44. The second opening 31d is provided at an end portion of the casing main-body portion 44 opposite to the side on which the first opening 31c is provided. The second opening 31d is formed larger than the chassis structure 30.

The lid 46 has a generally rectangular shape, and constitutes a wall portion of the casing 31 opposite to the side on which the distal end portion of the drug solution container 12 protrudes. The waterproof member 47 can be, for example, a waterproof tape, and is attached to a frame-shaped step 31e provided in the second opening 31d. The waterproof member 47 extends in a rectangular shape along the rectangular second opening 31d, and has a ring shape. By mounting the lid 46 to the second opening 31d of the casing main-body portion 44, the waterproof member 47 comes into contact with the lid 46 in a liquid-tight manner.

Next, the configuration of the plunger assembly 14A will be described in detail.

As illustrated in FIG. 3, the plunger assembly 14A includes the feed screw 48 driven by the drive mechanism 24, a first plunger 50 driven by the feed screw 48, a second plunger 52 driven by the feed screw 48, a nut member 54 held by the second plunger 52, and a base portion 56 that supports the second plunger 52.

The feed screw 48 includes a rod portion 58 and a driven gear 60 coupled to the rod portion 58 and driven by the drive gear 37. The rod portion 58 includes a male thread portion 62 having a male thread 62a formed on the outer periphery, and an extending portion 63 extending from the proximal end of the male thread portion 62 in the proximal direction, and wherein the extending portion 63 does not have the male thread formed on the outer periphery.

The male thread portion 62 is longer than the extending portion 63. The distal end portion of the male thread portion 62 is located inside the drug solution container 12. The outer diameter of the male thread portion 62 is greater (i.e. larger) than the outer diameter of the extending portion 63. The rod portion 58 further includes a coupling flange portion 64 provided at the proximal end of the extending portion 63. The coupling flange portion 64 includes a coupling concave portion 65a having a non-circular cross section on its proximal end surface, and is coupled (engaged) with a distal-end side shaft portion 60c of the driven gear 60 so as to be non-rotatable relatively (i.e., coupling flange portion and the distal-end side shaft portion 60c do not rotate relative to each other).

The driven gear 60 is rotatably arranged coaxially with the rod portion 58 and meshes with the drive gear 37 of the drive mechanism 24 (see, for example, FIG. 2). The driven gear 60 includes a gear portion 60b having a tooth portion 60a formed on an outer peripheral portion, the distal-end side shaft portion 60c protruding from the center of the distal end surface of the gear portion 60b in the distal direction, and a proximal-end side shaft portion 60d protruding from the center of the proximal end surface of the gear portion 60b in the proximal direction. The distal-end side shaft portion 60c and the proximal-end side shaft portion 60d are rotatably supported by the support member 39 of the chassis structure 30.

A coupling convex portion 65b having a non-circular cross section inserted into the coupling concave portion 65a provided in the coupling flange portion 64 of the rod portion 58 is provided at the distal end of the distal-end side shaft portion 60c. A spring 66 that elastically urges the driven gear 60 in the distal direction is arranged between a support piece 39a of the support member 39 and the gear portion 60b.

Figure 6:
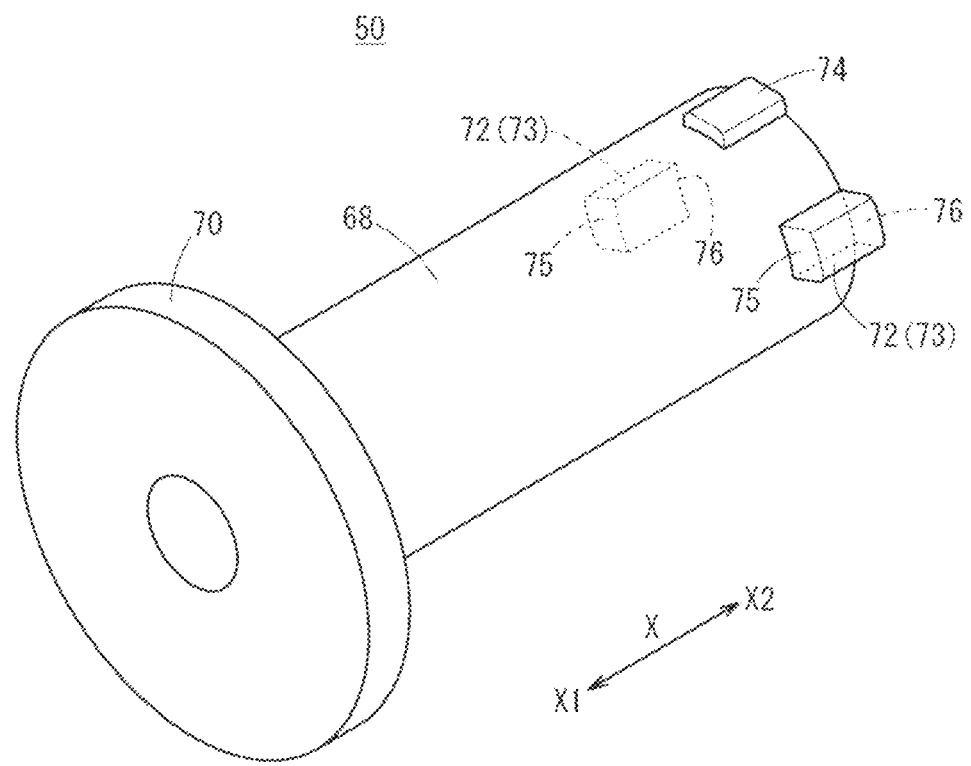
FIG. 6 is a perspective view of a first plunger.

As illustrated in FIG. 6, the first plunger 50 includes a hollow first cylindrical body portion 68, an annular first distal-end flange 70 protruding radially outward from the distal end of the first cylindrical body portion 68, first protrusion portions 72 protruding radially outward from a proximal-end outer peripheral surface of the first cylindrical body portion 68, and support protrusions 74 protruding radially outward from the proximal-end outer peripheral surface of the first cylindrical body portion 68 at a circumferential position different from the first protrusion portions 72.

As illustrated in FIG. 3, on the inner peripheral surface of the proximal end of the first cylindrical body portion 68, there is a first female thread portion 68a threadedly engaged with the male thread portion 62 of the first plunger 50 at least in an initial state before the plunger assembly 14A starts the extension operation.

The first distal-end flange 70 is a flange portion that is capable of being held in abutment (i.e., abuts or borders) against the inner peripheral surface of the drug solution container 12. The distal end surface of the first distal-end flange 70 is a gasket pressing portion 71 that is capable of pressing the gasket 22. In the initial state of the drug solution dosage device 10, the gasket pressing portion 71 is separated from the gasket 22 by a small distance.

In FIG. 6, the first protrusion portions 72 each constitute a first guided portion 73 guided by a first guide portion 86 (FIG. 7A) described later of the second plunger 52. The distal end surface of each of the first protrusion portions 72 constitutes a first engagement portion 75 that is engageable with a second engagement portion 98 (FIG. 7A) described later of the second plunger 52. The proximal end surface of each of the first protrusion portions 72 constitutes a first abutment portion 76 that is capable of being held in abutment against a second abutment portion 53 (FIG. 7B) described later of the second plunger 52.

In the initial state of the drug solution dosage device 10, the support protrusions 74 support temporary locking claw portions 85a (FIG. 7A) described later of the second plunger 52 from inside of the second plunger 52.

Figure 7A:
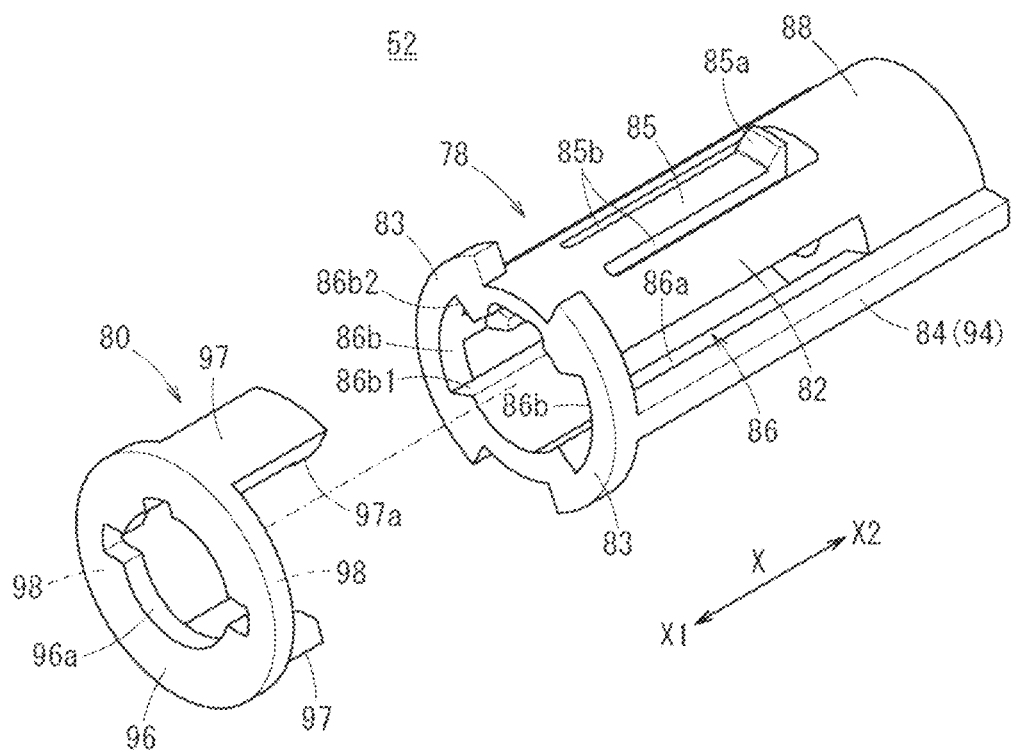
FIG. 7A is an exploded perspective view of a second plunger.

As illustrated in FIG. 7A, the second plunger 52 includes a plunger main-body portion 78 and a cap member 80 fixed to the plunger main-body portion 78. The plunger main-body portion 78 includes a hollow second cylindrical body portion 82, a pair of second distal-end flanges 83 protruding radially outward from the distal end of the second cylindrical body portion 82, and second protrusion portions 84 protruding radially outward from the outer surface of the second cylindrical body portion 82 and extending in the axial direction.

The second cylindrical body portion 82 is provided with temporary locking elastic pieces 85 such that the second cylindrical body portion 82 is elastically deformable in the radial direction. An end portion (free end portion) of each of the temporary locking elastic pieces 85 is provided with the temporary locking claw portion 85a protruding outward. The second cylindrical body portion 82 is provided with first guide portions 86. The first guide portions 86 are each engaged with the first guided portion 73 of the first plunger 50, and configured to prevent the rotation of the first plunger 50 with respect to the second plunger 52, and configured to guide movement of the first plunger 50 in the axial direction. The second distal-end flanges 83 extend in an arc shape. A notch-shaped gap is formed between the pair of second distal-end flanges 83.

Figure 7B:
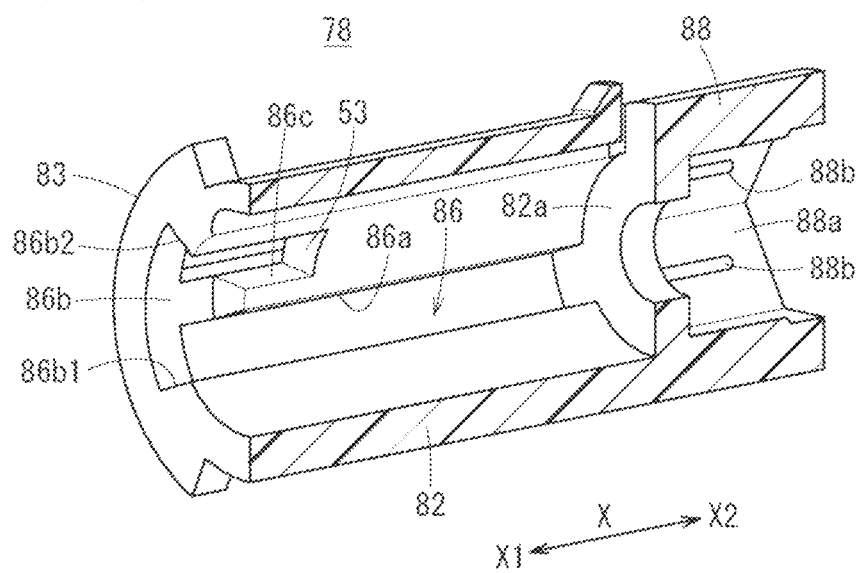
FIG. 7B is a perspective cross-sectional view of a plunger main-body portion of a second plunger.

As illustrated in FIG. 7B, the first guide portions 86 each include an axial guide 86a that extends along the axial direction and guide the first guided portion 73 (FIG. 6) of the first plunger 50 in the axial direction, and a rotation guide 86b that is continuous with the distal end of the axial guide 86a and extends in the circumferential direction to guide the first guided portion 73 in the circumferential direction. The rotation guides 86b each include a first end portion 86b1 continuous with the axial guide 86a, and a second end portion 86b2 different from the first end portion 86b1.

The first guide portions 86 each further include a lock portion 86c that is continuous with the second end portion 86b2 of the rotation guide 86b. The lock portions 86c each extend from the second end portion 86b2 in the proximal direction with a length shorter than the axial guide 86a, and are each capable of locking the first guided portion 73 of the first plunger 50.

Figure 8A:
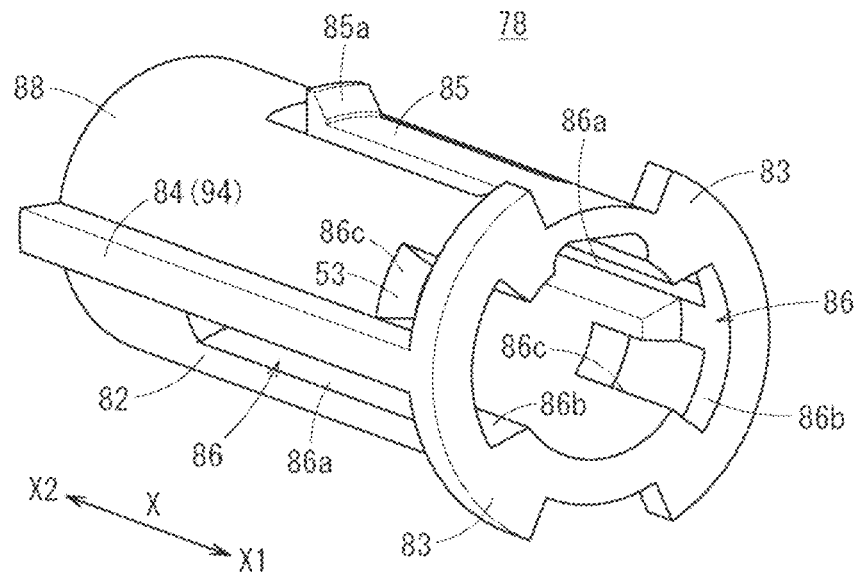
FIG. 8A is a perspective view of the plunger main-body portion of the second plunger as viewed from a distal end side.

In the present embodiment, as illustrated in FIG. 8A, the axial guides 86a are hole portions penetrating the peripheral wall portion of the second cylindrical body portion 82 in the wall thickness direction, and the two axial guides 86a are provided at positions opposite to each other with the axis of the second cylindrical body portion 82 as a reference. The two rotation guides 86b are provided at positions opposite to each other with the axis of the second cylindrical body portion 82 as a reference. The lock portions 86c are hole portions penetrating the peripheral wall portion of the second cylindrical body portion 82 in the wall thickness direction, and the two lock portions 86c are provided at positions opposite to each other with the axis of the second cylindrical body portion 82 as a reference. The proximal end surface of each of the lock portions 86c constitutes the second abutment portion 53 that is capable of being held in abutment against the first abutment portion 76 (FIG. 6) of the first plunger 50.

Figure 8B:
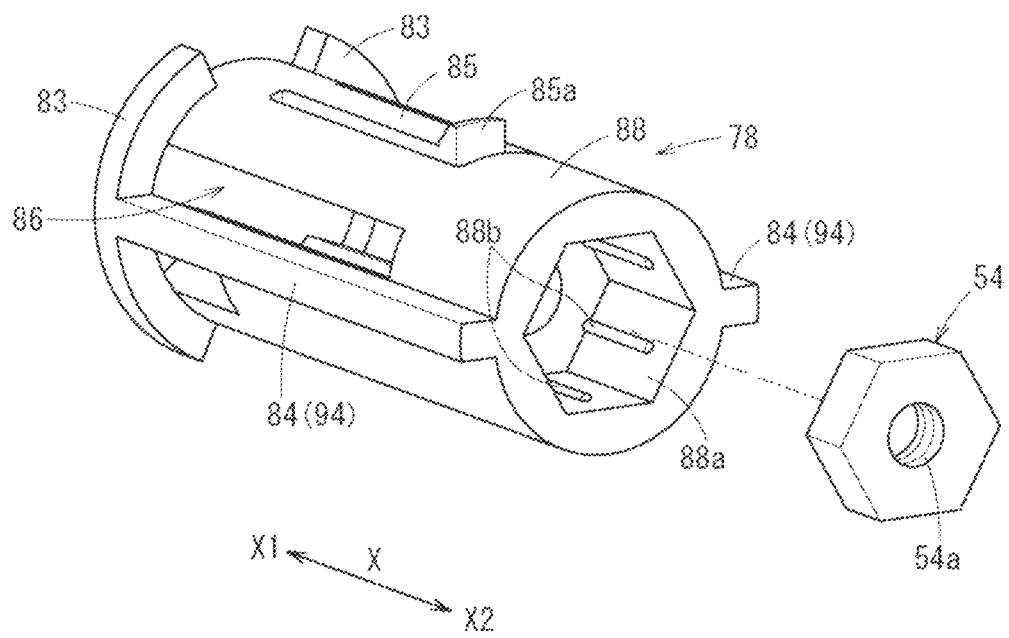
FIG. 8B is a perspective view of the plunger main-body portion of the second plunger as viewed from a proximal end side.

As illustrated in FIG. 8B, a nut accommodating portion 88 is provided at a proximal end portion of the second cylindrical body portion 82. The nut accommodating portion 88 accommodates the nut member 54 so that the nut member 54 is non-rotatable and movable in the axial direction (i.e., the nut member 54 is not rotatable nor movable in the axial direction). The inner peripheral shape of the nut accommodating portion 88 is formed in a hexagonal shape in accordance with the outer diameter of the nut member 54. A plurality of ribs 88b extending along the axial direction and arranged at intervals in the circumferential direction are formed on an inner peripheral surface 88a of the nut accommodating portion 88, and the plurality of ribs 88b are held in abutment against the outer peripheral surface of the nut member 54.

As illustrated in FIG. 3, the nut accommodating portion 88 includes a distal-end pedestal portion 89 and a proximal-end pedestal portion 90. The distal-end pedestal portion 89 is a proximal end surface of an inner peripheral protruding wall 82a (see also FIG. 7B) having a hole portion, which is provided inside the second cylindrical body portion 82. The proximal-end pedestal portion 90 is a distal end surface of a pedestal member 82b fixed inside the proximal end of the second cylindrical body portion 82.

A nut urging member 92 that urges the nut member 54 in the distal direction is arranged in the nut accommodating portion 88. In the present embodiment, the nut urging member 92 is a coil spring. The rod portion 58 of the feed screw 48 is inserted into the nut urging member 92.

In the initial state of the plunger assembly 14A, the distal end surface of the nut member 54 is held in abutment against the distal-end pedestal portion 89, the distal end of the nut urging member 92 is held in abutment against the proximal end surface of the nut member 54, and the proximal end of the nut urging member 92 is held in abutment against the proximal-end pedestal portion 90.

In FIG. 8A, the second protrusion portions 84 each constitute a second guided portion 94 guided by a second guide portion 100 (FIG. 9) described later of the base portion 56. The second protrusion portions 84 each extend in the axial direction over substantially the overall length of the second cylindrical body portion 82, and are each provided between the axial guide 86a and the lock portion 86c of the first guide portion 86. The distal end of each of the second protrusion portions 84 is continuous with the second distal-end flange 83. In the present embodiment, as illustrated in FIG. 8B, the two second protrusion portions 84 are provided at positions opposite to each other with the axis of the second cylindrical body portion 82 as a reference.

As illustrated in FIG. 3, the cap member 80 is fixed to the distal end of the plunger main-body portion 78. In FIG. 7A, the cap member 80 includes a distal-end ring portion 96 having an opening 96a, and a pair of coupling arms 97 protruding in the proximal direction from the outer rim of the proximal end surface of the distal-end ring portion 96. The first cylindrical body portion 68 (FIG. 6) of the first plunger 50 is inserted into the opening 96a of the distal-end ring portion 96. The outer peripheral portion of the distal-end ring portion 96 is a distal-end outer peripheral portion that is capable of being held in abutment against the inner peripheral surface of the drug solution container 12. The proximal end surface of the distal-end ring portion 96 includes second engagement portions 98 that is engageable with the first engagement portions 75 of the first plunger 50.

A free end portion of each of the coupling arms 97 is provided with an engagement claw 97a protruding inward (i.e., in the proximal direction (direction of the arrow X2)). The engagement of the engagement claws 97a with distal ends of slits 85b formed on both sides of the temporary locking elastic pieces 85 prevents the cap member 80 from being disengaged from the plunger main-body portion 78.

As illustrated in FIG. 3, in the nut member 54, a second female thread portion 54a that is capable of being threadedly engaged with the male thread portion 62 of the feed screw 48 is formed on the inner periphery, and the feed screw 48 is inserted in the inner periphery. The extending portion 63 of the feed screw 48 is inserted into the nut member 54 in an initial state. The nut member 54 has a hexagonal outer shape. Note that the nut member 54 may have a non-circular outer shape such as another polygonal shape.

Figure 9:
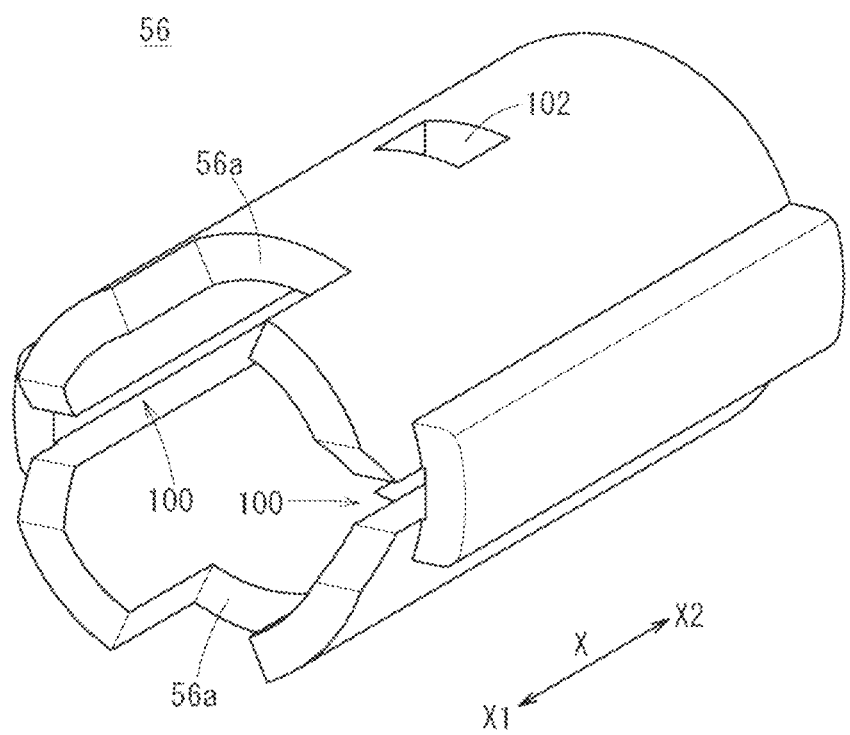
FIG. 9 is a perspective view of a base portion.

As illustrated in FIG. 2, the base portion 56 is fixed to the chassis structure 30. As illustrated in FIG. 9, the base portion 56 is a hollow member, and includes the groove-shaped second guide portions 100 extending in the axial direction. In the present embodiment, the two second guide portions 100 are provided at positions opposite to each other with the axis of the base portion 56 as a reference. The second guide portions 100 are each engaged with a second guided portion 94 (for example, FIG. 7A) of the second plunger 52, prevent the rotation of the second plunger 52 with respect to the feed screw 48, and guide axial movement of the second plunger 52.

The base portion 56 includes temporary locking concave portions 102 into which the temporary locking claw portions 85a (for example, FIG. 7A) of the second plunger 52 are disengageably inserted. In the present embodiment, the temporary locking concave portions 102 have a form of a hole penetrating the peripheral wall portion of the base portion 56 in the thickness direction. Note that the temporary locking concave portions 102 may be grooves provided on the inner peripheral surface of the base portion 56. Notches 56a into which the coupling arms 97 (FIG. 7A) of the cap member 80 are inserted are provided at the distal end of the base portion 56.

The drug solution dosage device 10 configured as described above is assembled, for example, by the following procedure.

Figure 10A:
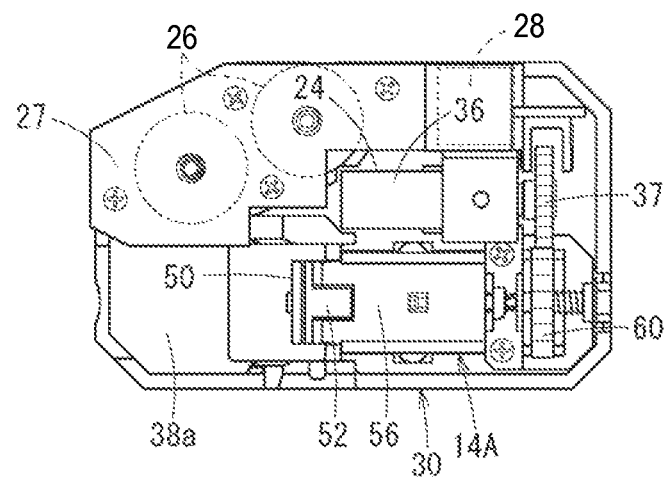
FIG. 10A is a first explanatory view of a method for assembling the drug solution dosage device.

As illustrated in FIG. 10A, the plunger assembly 14A, the drive mechanism 24, and the electric board 27 to which the control unit 28 and the batteries 26 are attached are assembled (fixed) at predetermined positions of the chassis structure 30.

Figure 10B:
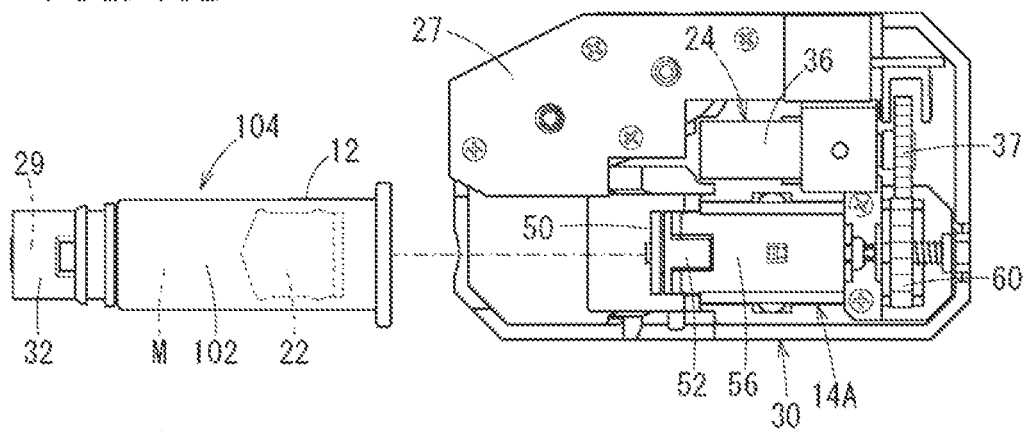
FIG. 10B is a second explanatory view of the method for assembling the drug solution dosage device.

Next, as illustrated in FIG. 10B, a prefilled syringe 104 is assembled to the chassis structure 30. The prefilled syringe 104 is an assembly in which the sealing member 29 and the fixing cap 32 are mounted to the distal end portion of the drug solution container 12, the drug solution M is filled in the drug solution container 12, and the gasket 22 is inserted into the drug solution container 12.

Figure 10C:
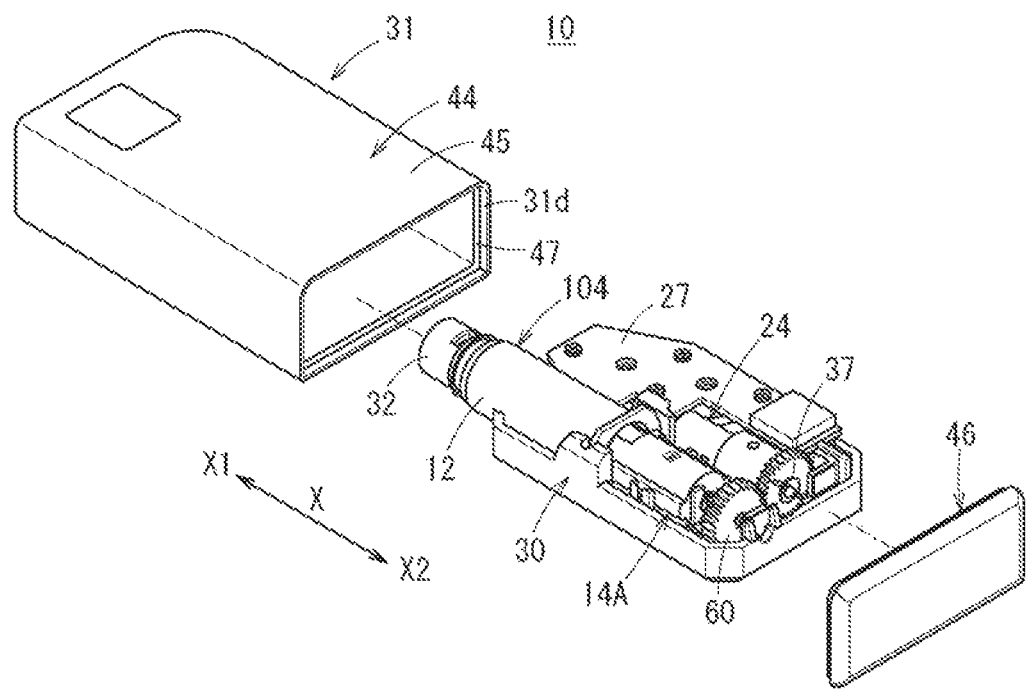
FIG. 10C is a third explanatory view of the method for assembling the drug solution dosage device.

Next, as illustrated in FIG. 10C, the chassis structure 30 to which the plunger assembly 14A and the like are assembled is inserted into the casing main-body portion 44 through the second opening 31d of the casing main-body portion 44. At this time, the drug solution container 12 is inserted into the waterproof packing 42 (FIG. 4) arranged in the first opening 31c of the casing main-body portion 44, and the waterproof packing 42 is in close contact with the outer peripheral surface of the drug solution container 12 in a liquid-tight manner. Next, the second opening 31d of the casing main-body portion 44 is closed with the lid 46. At this time, the lid 46 is in close contact with the waterproof member 47 arranged in the second opening 31d of the casing main-body portion 44 in a liquid-tight manner. Thereby, a waterproof structure is constructed.

Next, the operation of the drug solution dosage device 10 configured as described above will be described.

When the feed screw 48 rotates by the drive mechanism 24 (FIG. 2) from the initial state illustrated in FIGS. 3 and 11, the first plunger 50 threadedly engaged with the male thread portion 62 of the feed screw 48 moves forward (i.e., in a distal direction). At this time, since the first guided portions 73 (FIG. 6) are guided by the first guide portions 86 (FIG. 7A), the first plunger 50 moves forward with its rotation restricted. On the other hand, since the temporary locking claw portions 85a of the second plunger 52 are inserted into the temporary locking concave portions 102 of the base portion 56, and the male thread portion 62 of the feed screw 48 is not threadedly engaged with the nut member 54 (the extending portion 63 of the feed screw 48 is inserted into the nut member 54), the second plunger 52 does not move forward even when the feed screw 48 rotates.

Figure 12:
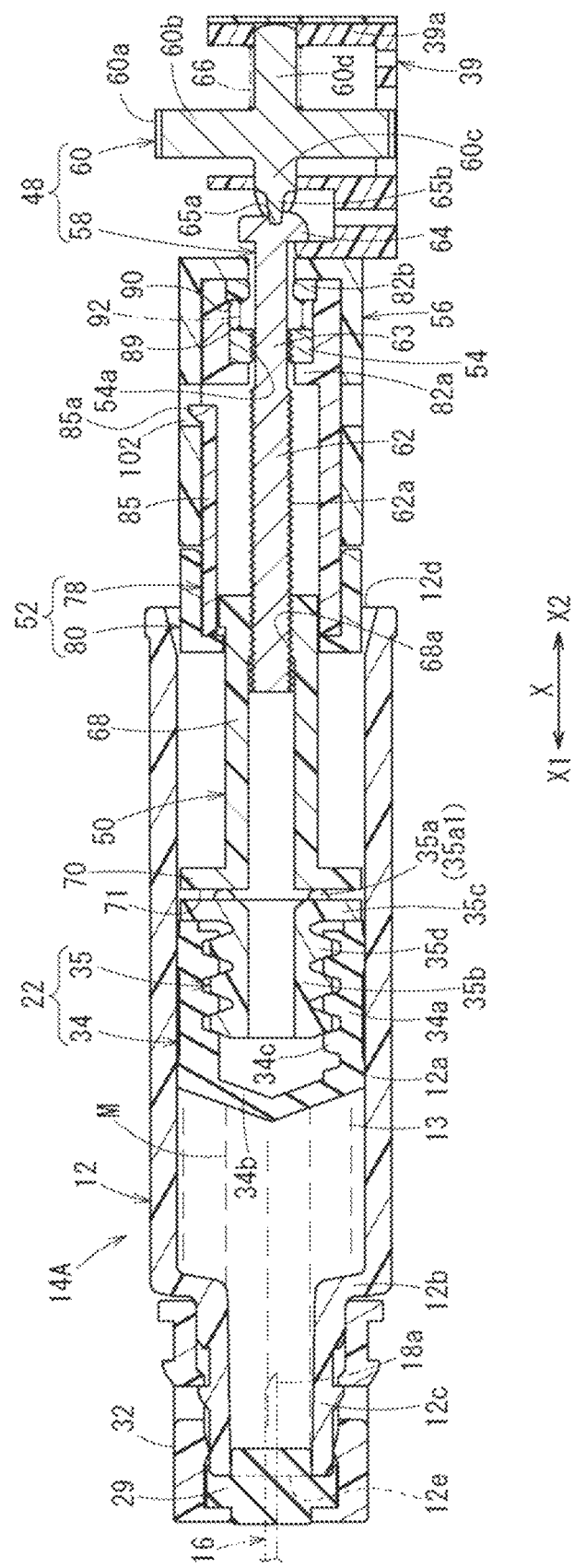
FIG. 12 is a second view illustrating the operation of the plunger assembly.
Figure 13A:
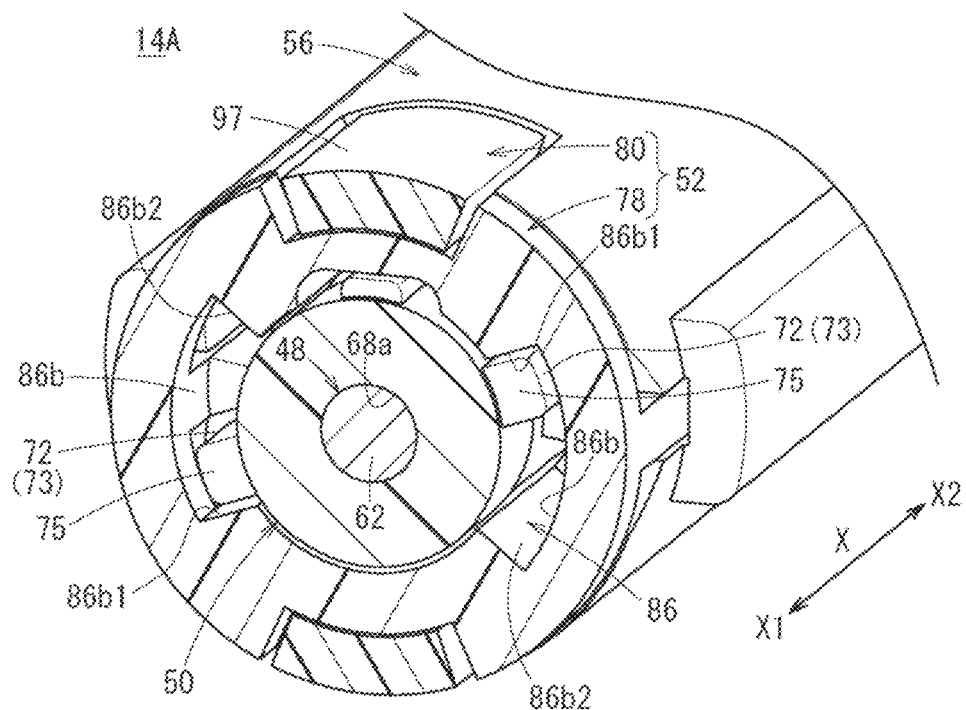
FIG. 13A is a third view illustrating the operation of the plunger assembly.

As illustrated in FIG. 12, when the first plunger 50 moves forward to the vicinity of the distal end of the second plunger 52 with the rotation of the feed screw 48, the first plunger 50 rotates by a predetermined angle in accordance with the rotation of the feed screw 48. Specifically, as illustrated in FIG. 13A, when the first guided portions 73 of the first plunger 50 reach the rotation guides 86b provided at the distal ends of the first guide portions 86 of the second plunger 52 (are disengaged from the axial guides 86a), the first plunger 50 is rotatable with respect to the second plunger 52. For this reason, the first plunger 50 in which the first guided portions 73 have reached the rotation guides 86b moves so as to follow the feed screw 48 only while the first guided portions 73 move from the first end portions 86b1 to the second end portions 86b2 of the rotation guides 86b.

Figure 13B:
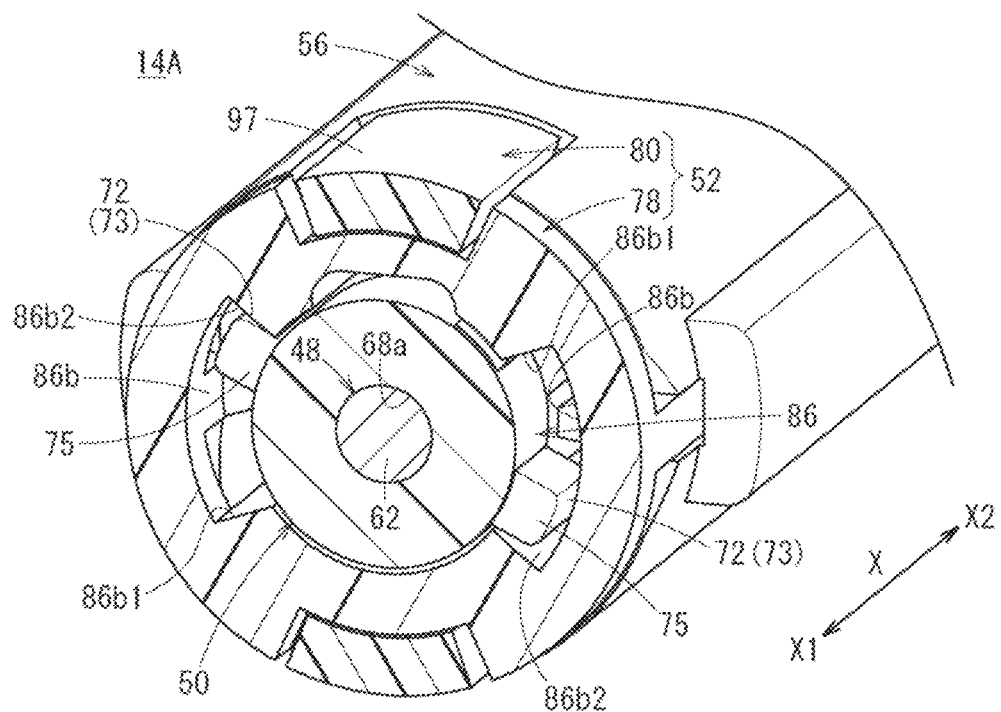
FIG. 13B is a fourth view illustrating the operation of the plunger assembly.

Then, as illustrated in FIG. 13B, when the first guided portions 73 come into abutment against the second end portions 86b2 of the rotation guides 86b, the relative rotation of the first plunger 50 with respect to the second plunger 52 is restricted again. Accordingly, with the rotation of the feed screw 48, the first plunger 50 starts to move forward again, and the first engagement portions 75 of the first plunger 50 (distal end surfaces of the first protrusion portions 72) are engaged with the second engagement portions 98 of the second plunger 52 (proximal end surface of the distal end ring of the cap member 80) (FIG. 7A).

Then, when the first plunger 50 moves forward with the first engagement portions 75 of the first plunger 50 and the second engagement portions 98 of the second plunger 52 engaged with each other, as illustrated in FIG. 14, the first plunger 50 causes the second plunger 52 to move forward. That is, with the rotation of the feed screw 48, the first plunger 50 moves forward while pulling the second plunger 52. At this time, the temporary locking claw portions 85a of the second plunger 52 come off the temporary locking concave portions 102 of the base portion 56. With the forward movement of the second plunger 52, the male thread portion 62 of the feed screw 48 is threadedly engaged with the nut member 54 arranged on the second plunger 52.

Figure 15A:
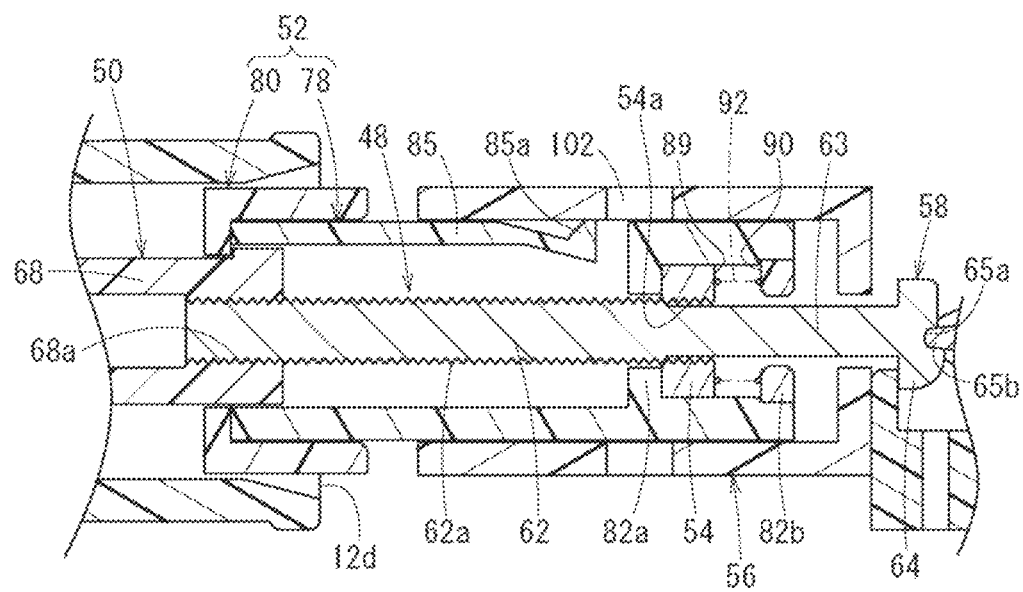
FIG. 15A is a sixth view illustrating the operation of the plunger assembly.
Figure 15B:
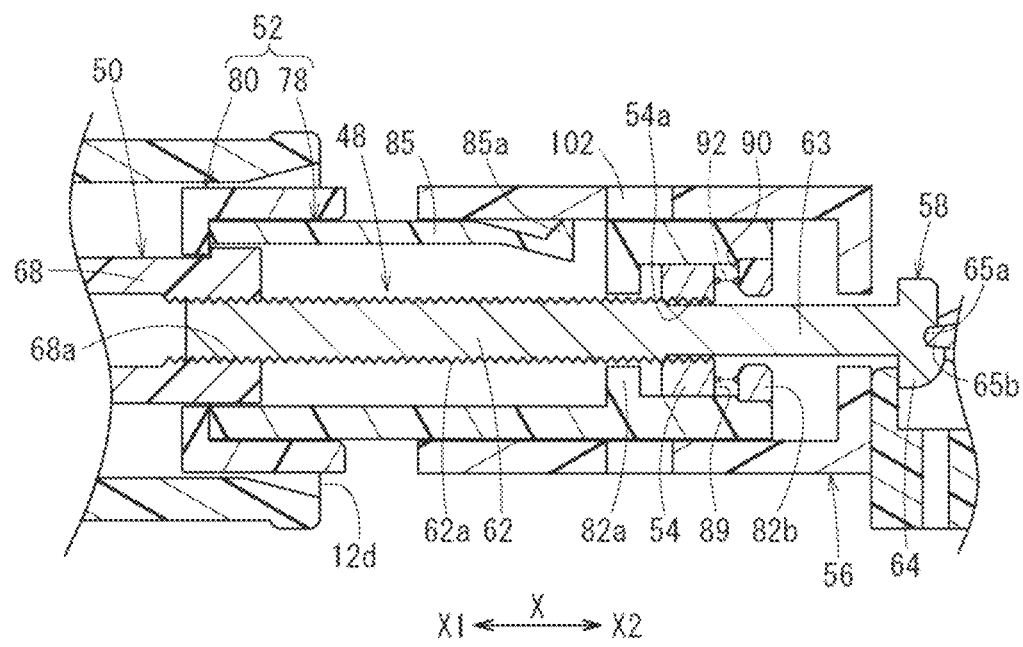
FIG. 15B is a seventh view illustrating the operation of the plunger assembly.

Specifically, when the second plunger 52 starts to move forward, as illustrated in FIG. 15A, the proximal end of the male thread portion 62 comes into contact with the distal end of the second female thread portion 54a of the nut member 54. Even when the second female thread portion 54a does not mesh with the male thread portion 62 at the same time as this contact, since the nut member 54 is slidable relatively in the axial direction within the nut accommodating portion 88, as illustrated in FIG. 15B, the second plunger 52 can move forward by following the first plunger 50. At this time, the nut member 54 moves in the proximal direction relative to the second plunger 52 moving forward, against the urging force of the nut urging member 92.

When the phase of the male thread portion 62 and the phase of the second female thread portion 54a match with each other during forward movement of the second plunger 52 while the nut member 54 is urged in the distal direction by the nut urging member 92, the feed screw 48 and the nut member 54 are threadedly engaged with each other. When the meshing between the male thread portion 62 and the second female thread portion 54a is started, a double screw state is started, in which the male thread portion 62 of the feed screw 48 is threadedly engaged with both the first female thread portion 68a and the second female thread portion 54a.

Figure 16:
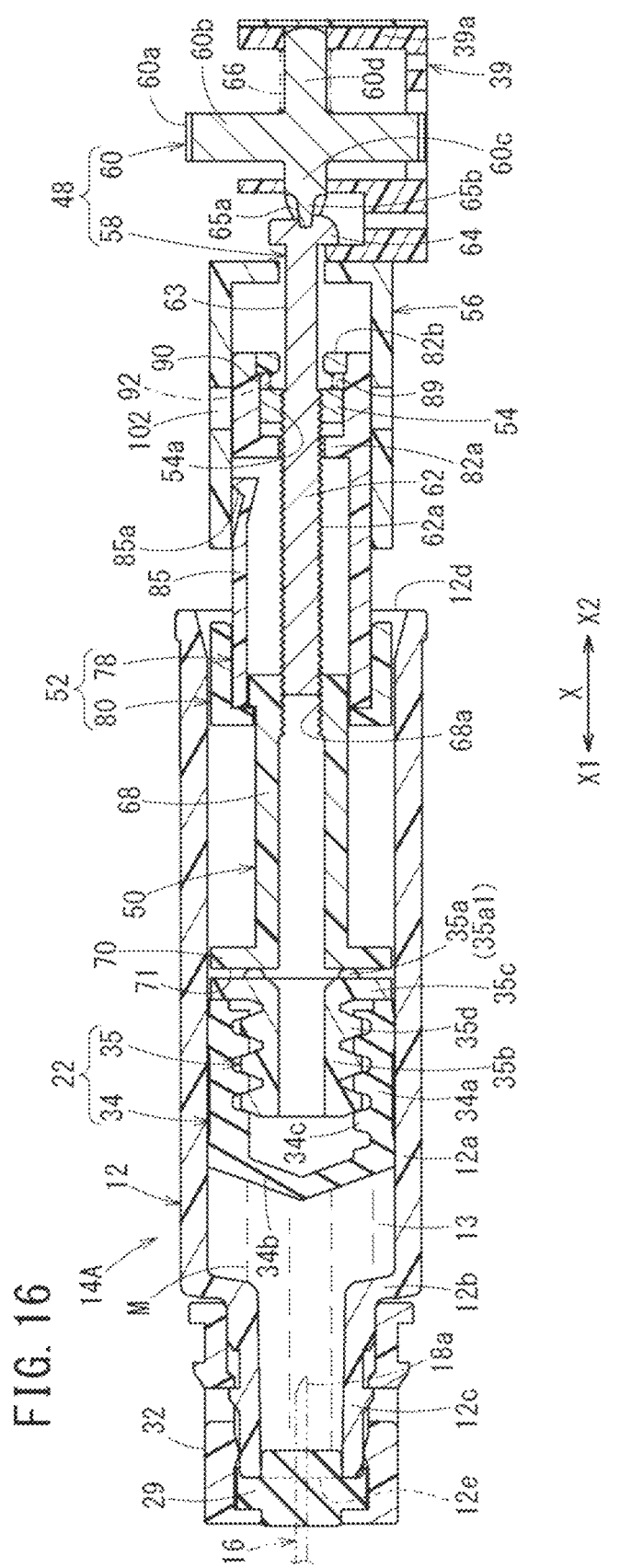
FIG. 16 is an eighth view illustrating the operation of the plunger assembly.

Then, as illustrated in FIG. 16, with the rotation of the feed screw 48, the first plunger 50 and the second plunger 52 move forward in the double screw state. At this time, since the distal end surface of the nut member 54 is separated from the distal-end pedestal portion 89 (FIG. 15B), the nut member 54 does not cause the second plunger 52 to move forward, but by the engagement between the first engagement portions 75 and the second engagement portions 98, the first plunger 50 causes the second plunger 52 to move forward. Note that the nut member 54, which has been brought into a rotation-restricted state by the nut accommodating portion 88, moves forward with the rotation of the feed screw 48 while maintaining the distance from the distal-end pedestal portion 89 (moves forward at the same speed as the second plunger 52).

Figure 17:
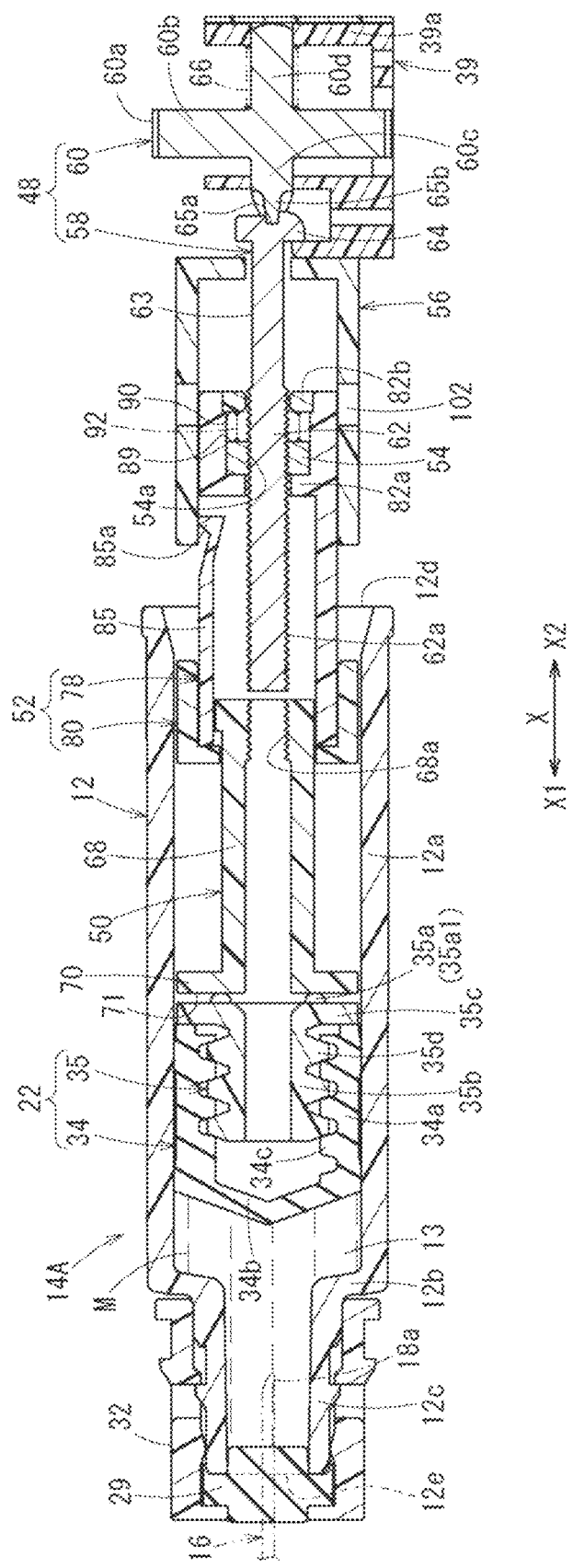
FIG. 17 is a ninth view illustrating the operation of the plunger assembly.

When the first plunger 50 and the second plunger 52 further move forward with the rotation of the feed screw 48, as illustrated in FIG. 17, the first female thread portion 68a of the first plunger 50 comes off the male thread portion 62 of the feed screw 48 (the thread engagement of the female thread portion 68a is released). When the thread engagement between the first plunger 50 and the feed screw 48 is released, the nut member 54 threadedly engaged with the feed screw 48 causes the second plunger 52 to move forward, and the second plunger 52 moving forward causes the first plunger 50 to move forward.

Figure 18:
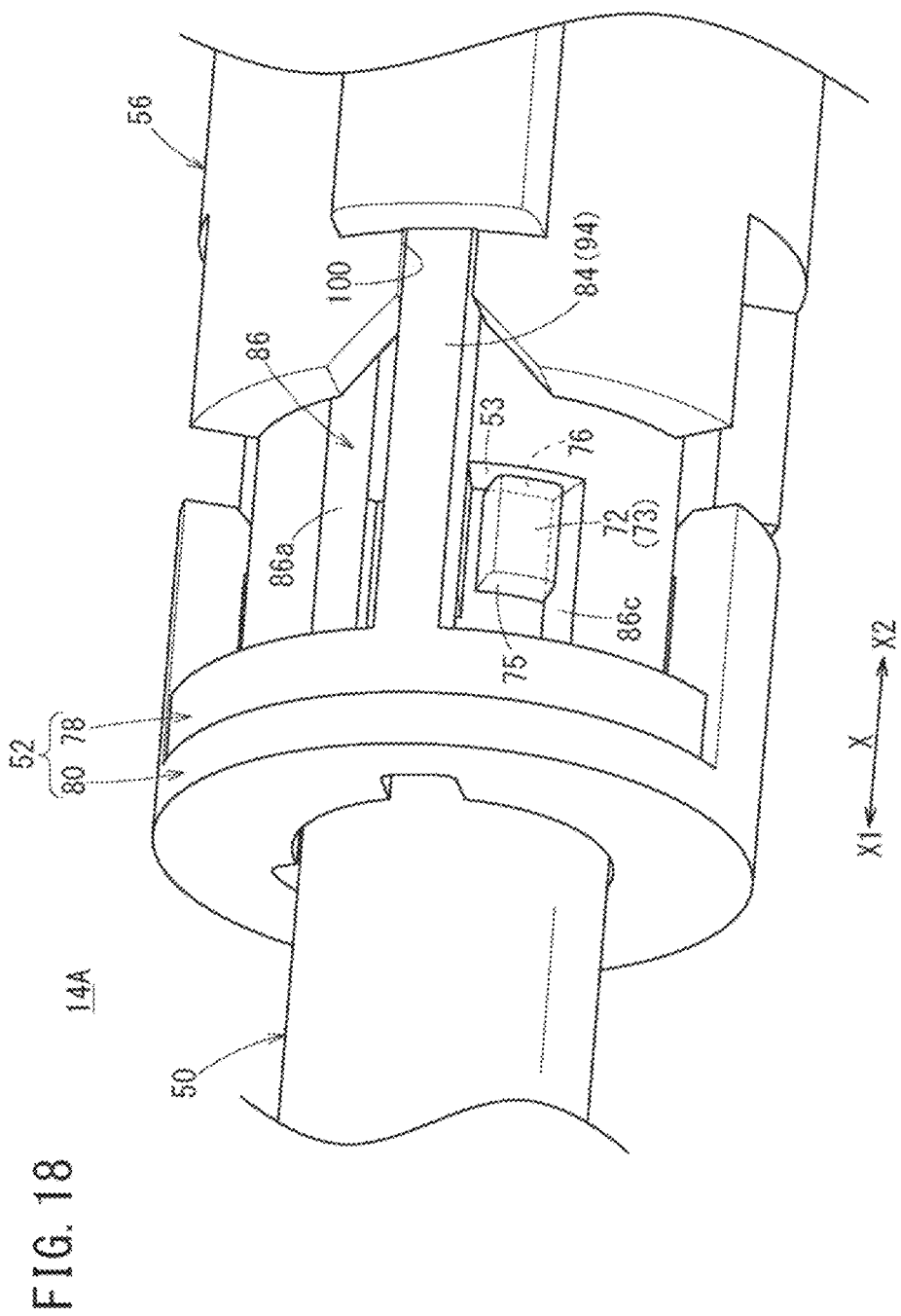
FIG. 18 is a tenth view illustrating the operation of the plunger assembly.

Specifically, when the thread engagement between the first plunger 50 and the feed screw 48 is released, the nut member 54 moves forward with the rotation of the feed screw 48, and comes into abutment against the distal-end pedestal portion 89 of the second plunger 52. Therefore, when the nut member 54 moving forward presses the distal-end pedestal portion 89 in the distal direction, the second plunger 52 starts to move forward. At this time, since the first plunger 50, which has been released from the thread engagement with the feed screw 48, is stopped, with the forward movement of the second plunger 52, as illustrated in FIG. 18, the second abutment portion 53 of the second plunger 52 comes into abutment against the first abutment portion 76 of the first plunger 50. Accordingly, the second abutment portion 53 of the second plunger 52 moving forward presses the first abutment portion 76 in the distal direction, whereby the first plunger 50 starts to move forward again. Accordingly, the first plunger 50 and the second plunger 52 move forward in a state where only the nut member 54 is threadedly engaged with the feed screw 48, and liquid is fed (i.e., from the drug solution container 12).

Figure 19:
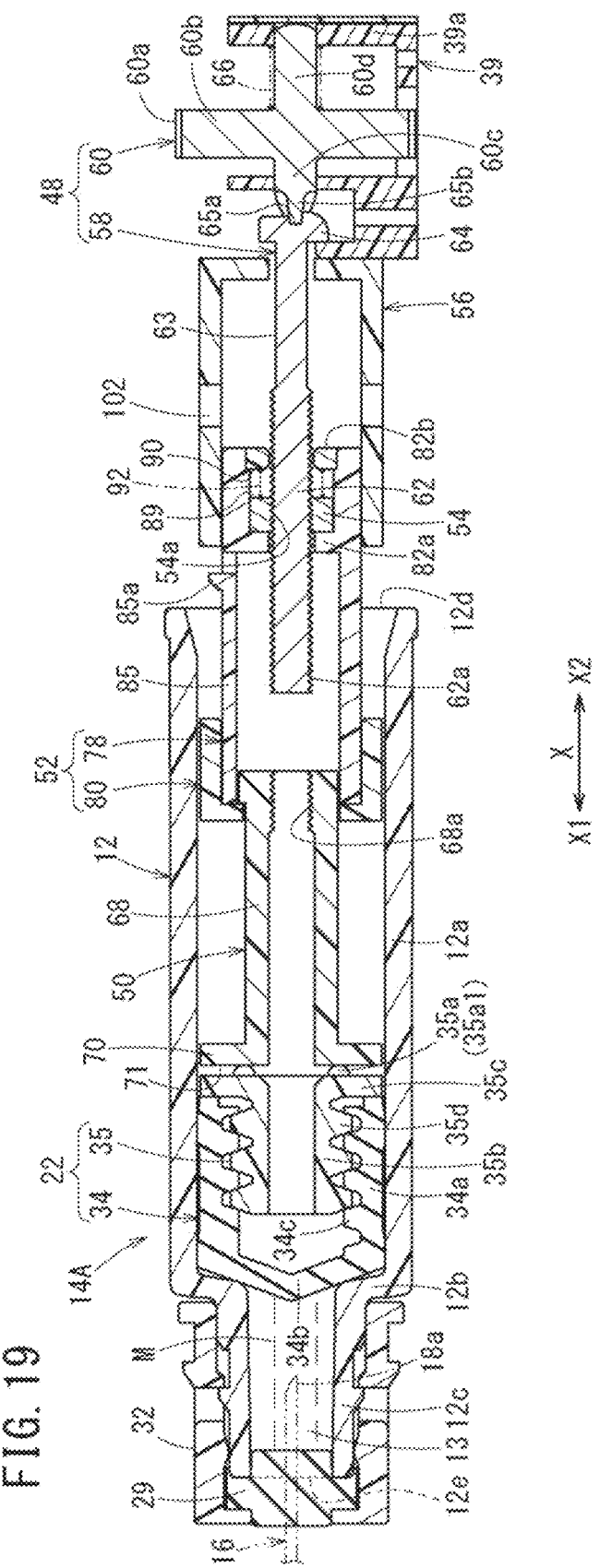
FIG. 19 is an eleventh view illustrating the operation of the plunger assembly.
Figure 20:
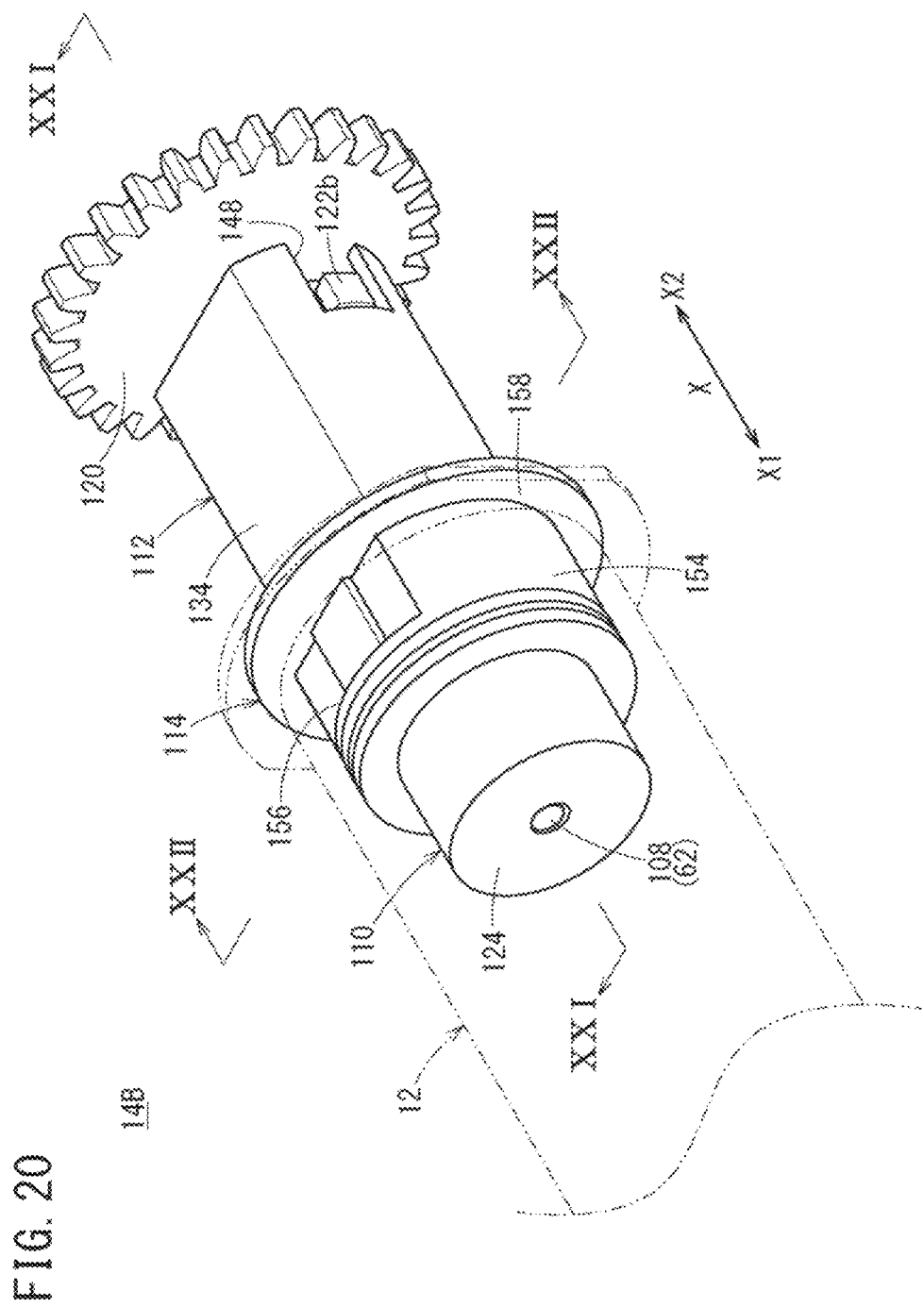
FIG. 20 is a perspective view of a plunger assembly according to another embodiment.

Then, as illustrated in FIG. 19, when the first plunger 50 and the second plunger 52 move forward to a position where the gasket 22 comes into abutment against the shoulder portion 12b of the drug solution container 12, the rotation of the feed screw 48 stops, and the liquid feed is completed.

In this case, the drug solution dosage device 10 including the plunger assembly 14A according to the present embodiment has the following effects.

The plunger assembly 14A includes the feed screw 48 including the male thread portion 62 and the extending portion 63, the first plunger 50 including the first female thread portion 68a, the second plunger 52 including the second female thread portion 54a, the nut member 54 that is assumingly movable in the axial direction with respect to the second plunger 52, and the base portion 56. After that, with the rotation of the feed screw 48, first, the first plunger 50 moves forward, and then the first plunger 50 moves forward while pulling the second plunger 52. Thereafter, the nut member 54 threadedly engaged with the feed screw 48, and then the second plunger 52 causes the first plunger 50 to move forward.

The plunger assembly 14A configured as described above extends in a plurality of stages, so that the overall length can be shortened, and accordingly, the drug solution dosage device 10 to which the plunger assembly 14A is mounted can be downsized. The downsizing of the device makes it possible to reduce the area required for application when the device is applied to a patient's body surface, so that the device can be rather easily applied to applications such as application to the patient's body surface. In addition, the downsizing of the device can improve usability such as carrying and storing of the device 10.

In addition, since the nut member 54 is movable in the axial direction relative to the second plunger 52, even when the male thread portion 62 of the feed screw 48 and the second female thread portion 54a of the nut member 54 do not mesh with each other at the same time as the contact between the male thread portion 62 of the feed screw 48 and the nut member 54, these can be threadedly engaged with each other when the phase of the male thread portion 62 and the phase of the second female thread portion 54a match with each other thereafter. Therefore, the second plunger 52 can be reliably caused to move forward through the nut member 54 by the feed screw 48.

The plunger assembly 14A includes the nut urging member 92 that urges the nut member 54 in the distal direction, and in the initial state, the distal end surface of the nut member 54 is held in abutment against the distal-end pedestal portion 89, the distal end of the nut urging member 92 is held in abutment against the proximal end surface of the nut member 54, and the proximal end of the nut urging member 92 is held in abutment against the proximal-end pedestal portion 90. With this configuration, since the nut member 54 is always urged in the distal direction, when the phase of the male thread portion 62 of the feed screw 48 and the phase of the second female thread portion 54a of the nut member 54 match with each other, the feed screw 48 and the nut member 54 can be threadedly engaged with each other reliably. That is, while the second plunger 52 moves forward by the pitch of the male thread portion 62, the feed screw 48 and the nut member 54 are always threadedly engaged with each other.

Note that the nut urging member 92 may not be provided. In the case wherein the nut urging member 92 is not provided, even if the meshing between the male thread portion 62 and the second female thread portion 54a fails several times while the second plunger 52 moves forward, the meshing can be achieved within the movable range of the nut member 54. Therefore, the second plunger 52 can be caused to move forward by the rotation of the feed screw 48.

The plurality of ribs 88b extending along the axial direction and arranged at intervals in the circumferential direction are formed on the inner peripheral surface of the nut accommodating portion 88, and the plurality of ribs 88b are held in abutment against the outer peripheral surface of the nut member 54. With this configuration, the sliding resistance of the nut member 54 with respect to the second plunger 52 can be reduced, and the relative axial movement of the nut member 54 with respect to the second plunger 52 can be relatively smooth.

The distal end of the first plunger 50 includes the flange portion that is capable of being held in abutment against the inner peripheral surface of the drug solution container 12. With this configuration, buckling of the first plunger 50 can be prevented.

The second plunger 52 includes the plunger main-body portion 78 including the nut accommodating portion 88, the first guide portions 86, the second guided portions 94, and the second abutment portions 53, and the cap member 80 fixed to the plunger main-body portion 78 and including the second engagement portions 98. With this configuration, the second plunger 52 including the first guide portions 86, the second guided portions 94, the second abutment portions 53, and the second engagement portions 98 can be rather easily manufactured by injection molding.

The cap member 80 has a distal-end outer peripheral portion that is capable of being held in abutment against the inner peripheral surface of the drug solution container 12. With this configuration, buckling of the second plunger 52 can be prevented.

The first guide portions 86 of the second plunger 52 each include the axial guide 86a that guides the first guided portion 73 of the first plunger 50 in the axial direction, and the rotation guide 86b that is continuous with the distal end of the axial guide 86a and guides the first guided portion 73 in the circumferential direction (FIG. 7B). With this configuration, the first plunger 50 can be rotated with the rotation of the feed screw 48 at the distal ends of the first guide portions 86.

The first guide portions 86 of the second plunger 52 each include the lock portion 86c that is continuous with the second end portion 86b2 of the rotation guide 86b (FIG. 7B). With this configuration, the first guided portions 73 are prevented from returning to the axial guides 86a of the first guide portions 86.

The second plunger 52 includes the temporary locking elastic pieces 85 each including the temporary locking claw portion 85a provided at the end portion of the temporary locking elastic pieces 85, and the base portion 56 includes the temporary locking concave portions 102 into which the temporary locking claw portions 85a are disengageably inserted. With this configuration, since the second plunger 52 is temporarily fixed to the base portion 56, the second plunger 52 can be prevented from moving forward by following the forward movement of the first plunger 50 before the feed screw 48 is threadedly engaged with the nut member 54.

The first plunger 50 includes the support protrusions 74 that each support the temporary locking claw portion 85a from inside. With this configuration, it is possible to prevent the temporary locking claw portions 85a from being disengaged from the temporary locking concave portions 102 until the first plunger 50 moves forward to some extent.

The casing 31 has the first opening 31c into which the drug solution container 12 is inserted. (FIG. 4). The drug solution container 12 has the distal end portion protruding from the casing 31 through the first opening 31c, and the ring-shaped waterproof packing 42 is arranged between the vicinity of the distal end portion of the drug solution container 12 and the casing 31. With this configuration, it is possible to prevent water from entering the casing 31 through the first opening 31c.

The casing 31 includes the casing main-body portion 44 including the accommodating portion 45 and the second opening 31d, the lid 46 that seals the second opening 31d, and the annular waterproof member 47 attached to the second opening 31d (FIG. 5). With this configuration, it is possible to prevent water from entering the casing 31 through the second opening 31d.

The drug solution dosage device 10 includes the chassis structure 30 in which the drug solution container 12, the drive mechanism 24, and the plunger assembly 14A are fixed at predetermined positions, respectively. Then, the chassis structure 30 is arranged in the casing 31, and the second opening 31d is formed to be larger than the chassis structure 30. With this configuration, for example, the plunger assembly 14A can be easily taken out of the casing 31 together with the chassis structure 30 through the second opening 31d.

The first plunger 50 is rotatable by a predetermined angle with respect to the second plunger 52 with the rotation of the feed screw 48 at the distal end of the first guide portion 86 of the second plunger 52 (FIGS. 13A and 13B). The gasket 22 includes the gasket main body 34 made of the first material having elasticity, and the abutment member 35 made of the second material harder than the first material and mounted to the proximal end of the gasket main body 34 (FIG. 3). The abutment member 35 includes the pressed portion 35a pressed by the gasket pressing portion 71. The gasket pressing portion 71 is made of a material harder than the first material. With this configuration, the sliding resistance of the first plunger 50 in the rotation direction with respect to the gasket 22 can be reduced. Therefore, the gasket 22 does not hinder the rotation of the first plunger 50.

The abutment member 35 includes the insertion portion 35b inserted into the gasket main body 34, and the proximal-end flange portion 35c provided at the proximal end of the insertion portion 35b. The proximal-end flange portion 35c includes the pressed portion 35a on the proximal end surface. The pressed portion 35a is a plurality of convex portions provided intermittently on the proximal end surface and protruding from the proximal end surface in the proximal direction. With this configuration, the sliding resistance of the first plunger 50 in the rotation direction with respect to the gasket 22 can be effectively reduced.

The plurality of convex portions of the pressed portion 35a, each have a dome shape that bulges toward the proximal end. With this configuration, the sliding resistance of the first plunger 50 in the rotation direction with respect to the gasket 22 can be more effectively reduced.

In the driving method of the plunger assembly 14A, with the rotation of the feed screw 48, the first plunger 50 moves forward in the axial direction (FIG. 11), the first engagement portions 75 of the first plunger 50 are engaged with the second engagement portions 98 of the second plunger 52, and the first plunger 50 moving forward causes the second plunger 52 to move forward (FIG. 14). Further, with the forward movement of the second plunger 52, the nut member 54 moves in the proximal direction relative to the second plunger 52 (FIG. 15B), and the movement of the nut member 54 causes the nut member 54 to be threadedly engaged with the male thread portion 62 of the feed screw 48 (FIG. 16). Then, the nut member 54 threadedly engaged with the male thread portion 62 moves forward with the rotation of the feed screw 48 to cause the second plunger 52 to move forward, and the second plunger 52 moving forward causes the first plunger 50 to move forward (FIG. 16). Thereby, the male thread portion 62 of the feed screw 48 and the second female thread portion 54a of the nut member 54 can be threadedly engaged with each other smoothly. Therefore, the second plunger 52 can be reliably moved forward through the nut member 54 by the feed screw 48.

In the driving method of the plunger assembly 14A, the nut member 54 is urged in the distal direction by the nut urging member 92. After the nut member 54 moves in the proximal direction relative to the second plunger 52 against the urging force of the nut urging member 92, the second female thread portion 54a of the nut member 54 is threadedly engaged with the male thread portion 62 of the feed screw 48 (see FIGS. 15B and 16). Thereby, the feed screw 48 and the nut member 54 can be reliably threadedly engaged with each other.

In the driving method of the plunger assembly 14A, the first plunger 50 restricted in rotation with respect to the feed screw 48 moves to the vicinity of the distal end of the second plunger 52 (FIG. 12), and the first plunger 50 that has moved to the vicinity of the distal end of the second plunger 52 rotates by a predetermined angle in accordance with the rotation of the feed screw 48 (FIGS. 13A and 13B). Further, the first plunger 50 that has rotated by the predetermined angle is restricted in rotation again, and the first engagement portions 75 of the first plunger 50 are engaged with the second engagement portions 98 of the second plunger 52. Then, the first plunger 50 in which the first engagement portions 75 are engaged with the second engagement portions 98 moves forward while pulling the second plunger 52 (FIG. 14). Accordingly, the second plunger 52 can be moved forward by the first plunger 50 moving forward with the rotation of the feed screw 48.

In the driving method of the plunger assembly 14A, in the state where the male thread portion 62 of the feed screw 48 is threadedly engaged with both the first female thread portion 68a and the second female thread portion 54a (double screw state), the feed screw 48 rotates, and the first plunger 50 and the second plunger 52 move forward (FIG. 16). Further, after the second plunger 52 moves forward by a predetermined length, the first female thread portion 68a of the first plunger 50 is disengaged from the male thread portion 62 (FIG. 17). Then, the second plunger 52 causes the first plunger 50 to move forward in a state where the first female thread portion 68a is disengaged from the male thread portion 62 and the second female thread portion 54a is threadedly engaged with the male thread portion 62. Thereby, the transition from the double screw state in which the male thread portion 62 of the feed screw 48 is threadedly engaged with both the first female thread portion 68a and the second female thread portion 54a to the state in which only the second female thread portion 54a and the male thread portion 62 are threadedly engaged with each other is performed relatively smoothly, and the first plunger 50 can be moved forward by the second plunger 52.

In the drug solution dosage device 10 described above, a plunger assembly 14B illustrated in FIG. 20 to FIG. 31 may be employed instead of the plunger assembly 14A. In the plunger assembly 14B, the same or similar components as those of the plunger assembly 14A are denoted by the same reference numerals, and detailed description of the same or similar components will be omitted.

Figure 21:
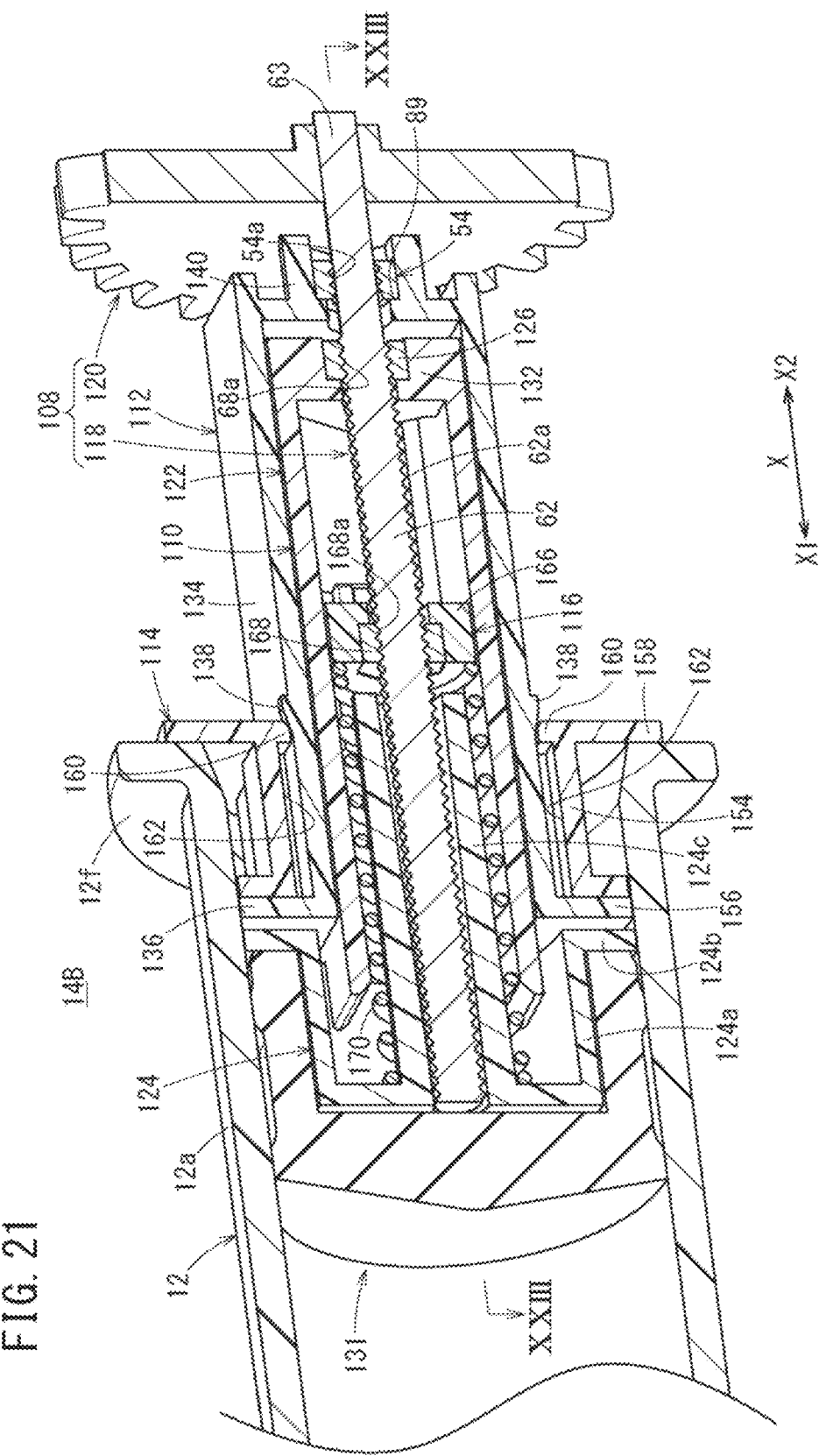
FIG. 21 is a cross-sectional view of the plunger assembly taken along the line XXI-XXI in FIG. 20.

As illustrated in FIG. 21, the plunger assembly 14B includes a feed screw 108 driven by the drive mechanism 24 (FIG. 2), a first plunger 110 driven in the distal direction by the feed screw 108, a second plunger 112 driven in the distal direction by the feed screw 108, the nut member 54 held by the second plunger 112, a base portion 114 that supports the second plunger 112, and a support mechanism 116 arranged inside the first plunger 110.

The feed screw 108 includes a rod portion 118 and a driven gear 120 coupled to the rod portion 118 and driven by the drive gear 37 (FIG. 2). The rod portion 118 includes the male thread portion 62 having the male thread 62a formed thereon, and the extending portion 63 extending from the proximal end of the male thread portion 62 in the proximal direction and not having the male thread formed thereon. The driven gear 120 is fixed to the proximal end of the extending portion 63 of the rod portion 118 so as to be non-rotatable relatively (i.e., the driven gear 120 and the extending portion do not rotate relative to each other), and meshes with the drive gear 37 (FIG. 2) of the drive mechanism 24.

The first plunger 110 includes a hollow first plunger main body 122 supported by the second plunger 112, a gasket pressing portion 124 fixed to the distal end of the first plunger main body 122, and a nut member 126 (hereinafter, referred to as "first nut member 126") fixed to the proximal end of the first plunger main body 122.

Figure 22:
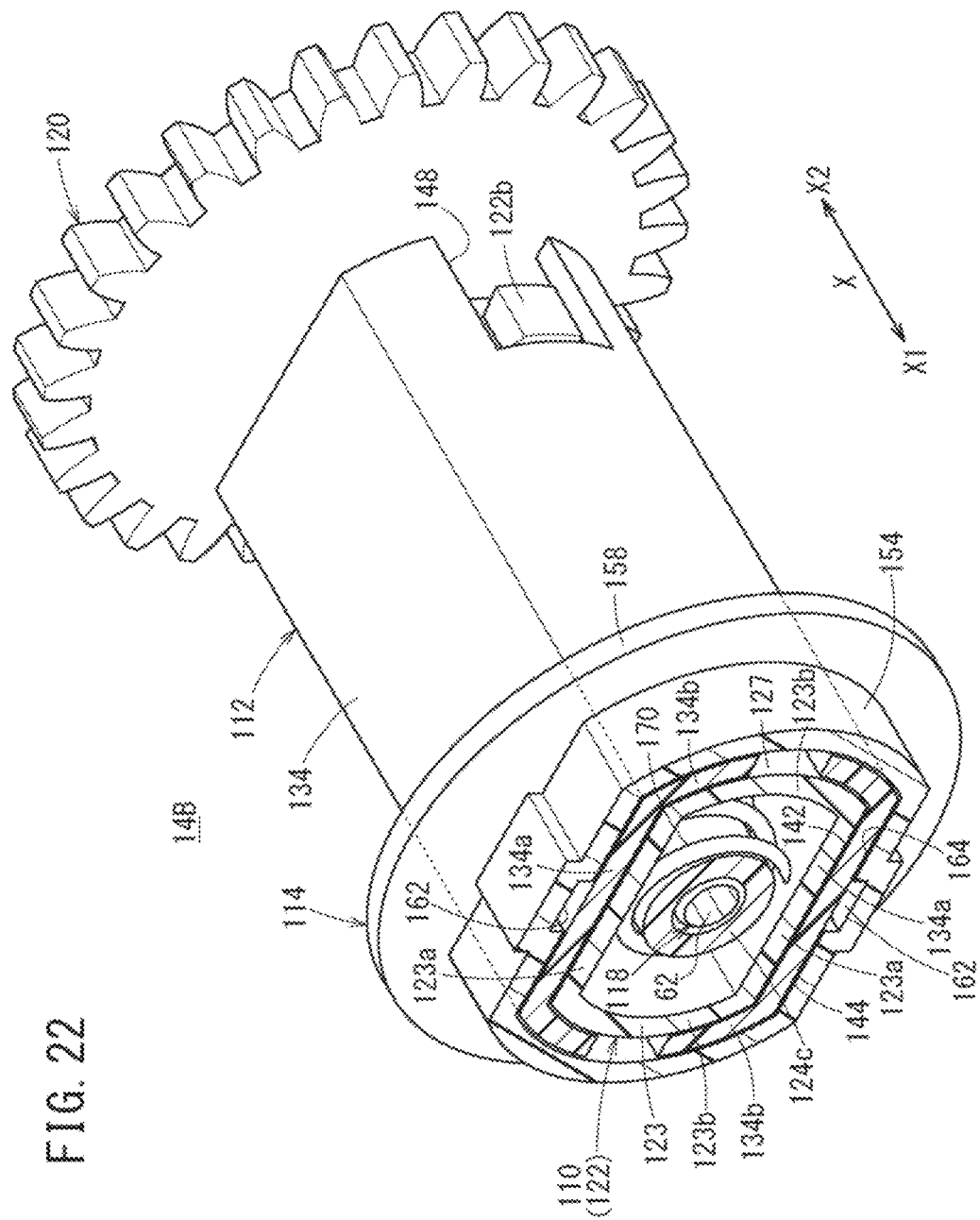
FIG. 22 is a cross-sectional view of the plunger assembly taken along line XXII-XXII in FIG. 20.

As illustrated in FIG. 22, a peripheral wall portion 123 of the first plunger main body 122 has a non-circular outer contour shape in a cross section perpendicular to the axial direction. Specifically, the peripheral wall portion 123 of the first plunger 110 includes a pair of flat wall portions 123a facing each other and a pair of arc-shaped wall portions 123b facing each other. The outer surface of the peripheral wall portion 123 of the first plunger 110 constitutes a first guided portion 127 guided by a first guide portion 142 of the second plunger 112.

Figure 23:
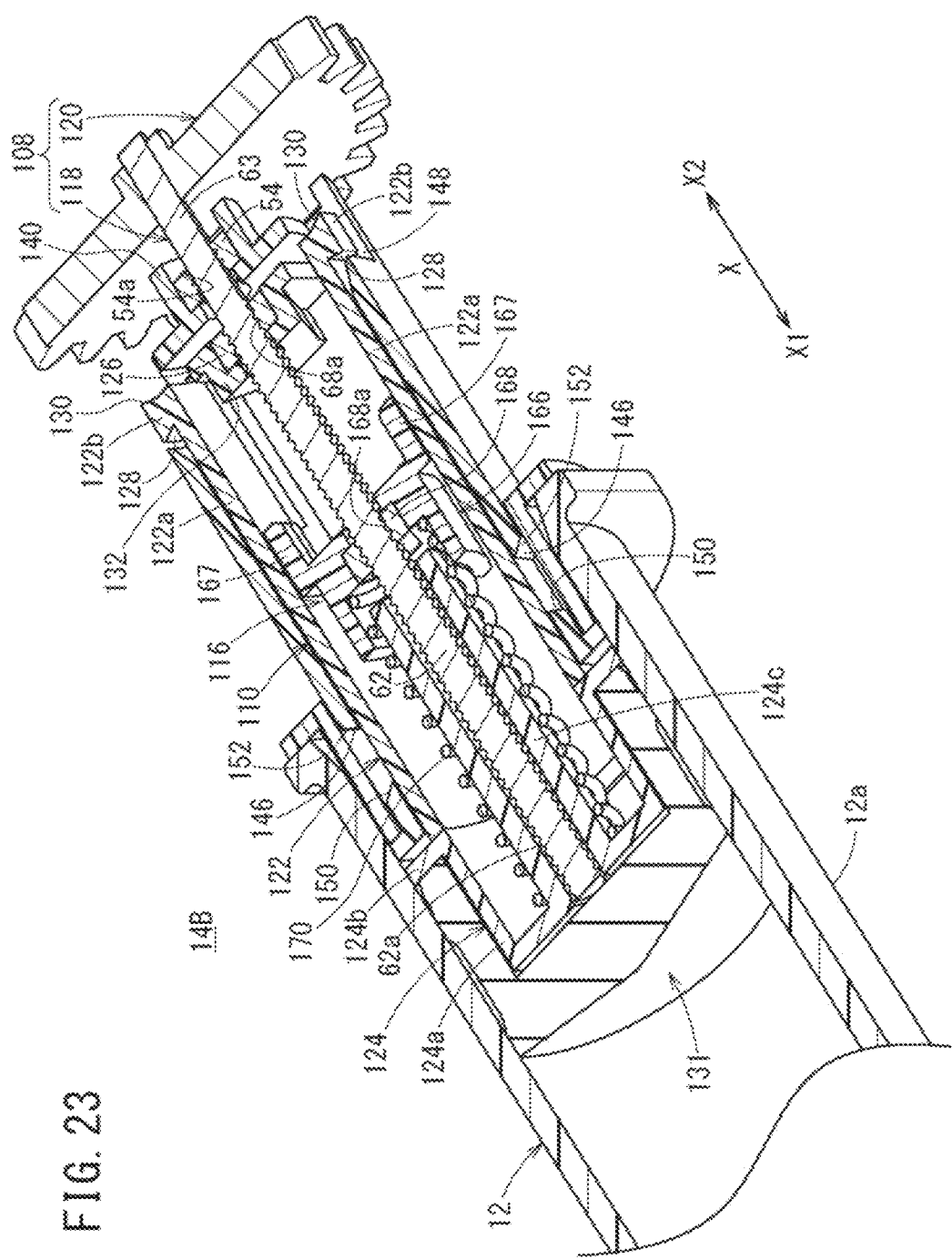
FIG. 23 is a cross-sectional view of the plunger assembly taken along line XXIII-XXIII in FIG. 21.

As illustrated in FIG. 23, the first plunger main body 122 is provided with engagement elastic pieces 122a that is elastically deformable inward and outward of the first plunger main body 122. The two engagement elastic pieces 122a are provided on sides opposite to each other with the axis of the first plunger main body 122 as a reference. At the proximal end (free end portion) of each of the engagement elastic pieces 122a, an outwardly protruding engagement claw portion 122b is provided. The distal end surface of each of the engagement claw portions 122b constitutes a first engagement portion 128 that is engageable with a second engagement portion 150 of the second plunger 112. The proximal end surface of each of the engagement claw portions 122b constitutes a first abutment portion 130 that is capable of being held in abutment against a second abutment portion 152 of the second plunger 112.

The gasket pressing portion 124 includes an insertion portion 124a inserted into the gasket 131, a proximal-end flange portion 124b protruding radially outward from a proximal end of the insertion portion 124a, and a hollow central cylindrical portion 124c protruding from the center of a distal-end wall portion of the insertion portion 124a in the proximal direction. The proximal-end flange portion 124b faces the proximal end surface of the gasket 131 and can be held in abutment against the inner peripheral surface of the drug solution container 12. The central cylindrical portion 124c protrudes in the proximal direction with respect to the proximal-end flange portion 124b. In the initial state of the plunger assembly 14B illustrated in FIG. 23, the male thread portion 62 of the feed screw 108 is inserted into the central cylindrical portion 124c.

The first nut member 126 is held (fixed) so as to be non-rotatable with respect to the first plunger main body 122 by a nut holding portion 132 provided inside the proximal end of the first plunger main body 122. The first female thread portion 68a is formed on an inner peripheral portion of the first nut member 126. Note that the first nut member 126 may be eliminated, and the first female thread portion 68a may be formed directly on the first plunger main body 122.

As illustrated in FIG. 21, the second plunger 112 includes a cylindrical body portion 134, a distal-end flange portion 136 protruding outward from a distal end of the cylindrical body portion 134, temporary locking claw portions 138 provided to an outer surface of the cylindrical body portion 134, and a nut accommodating portion 140 provided inside the proximal end of the cylindrical body portion 134. The two temporary locking claw portions 138 are provided on sides opposite to each other with the axis of the second plunger 112 as a reference. The temporary locking claw portions 138 each have an inclined surface that is inclined inward in the distal direction.

The nut member 54 (hereinafter, referred to as "second nut member 54") is accommodated in the nut accommodating portion 140 so as to be movable relatively in the axial direction. Note that, similarly to the plunger assembly 14A described above, the nut urging member 92 and the pedestal member 82b (for example, FIG. 3) may be arranged in the nut accommodating portion 140.

As illustrated in FIG. 22, the cylindrical body portion 134 of the second plunger 112 has a non-circular outer contour shape in a cross section perpendicular to the axial direction. Specifically, the cylindrical body portion 134 includes a pair of flat wall portions 134a facing each other and a pair of arc-shaped wall portions 134b facing each other. The inner surface of the cylindrical body portion 134 constitutes the first guide portion 142 that prevents the rotation of the first plunger 110 with respect to the second plunger 112 and guides the axial movement of the first plunger 110. The outer surface of the cylindrical body portion 134 constitutes a second guided portion 144 guided by a second guide portion 164 described later of the base portion 114.

As illustrated in FIG. 23, distal-end concave portions 146 are provided at the distal end of the cylindrical body portion 134 of the second plunger 112, and proximal-end concave portions 148 are provided at the proximal end of the cylindrical body portion 134. The distal-end concave portions 146 and the proximal-end concave portions 148 each penetrate the peripheral wall of the cylindrical body portion 134 in the thickness direction. The distal end surface of each of the distal-end concave portions 146 constitutes the second engagement portion 150 that is engageable with the first engagement portion 128 of the first plunger 110.

The second engagement portion 150 is inclined inward in the proximal direction. The proximal end surface of each of the distal-end concave portions 146 constitutes the second abutment portion 152 that is capable of being held in abutment against the first abutment portion 130 of the first plunger 110. The second abutment portion 152 is inclined inward in the distal direction. The distal end surface of each of the proximal-end concave portions 148 is inclined inward in the distal direction.

As illustrated in FIG. 21, the base portion 114 is a hollow member, and is fitted into the proximal-end opening 12d of the drug solution container 12. The base portion 114 includes a base-portion body 154, a fitting protrusion 156 protruding outward from a distal end of the base-portion body 154, a proximal-end flange 158 protruding outward in a radial direction from a proximal end of the base-portion body 154, and temporary locking protrusions 160 protruding inward in the radial direction from the proximal end of the base-portion body 154. The distal end surface of the proximal-end flange 158 is held in abutment against the proximal end surface of the drug solution container 12. The temporary locking claw portions 138 of the second plunger 112 are releasably engaged with the temporary locking protrusions 160.

On the inner surface of the base-portion body 154, there are provided groove portions 162 into which the temporary locking claw portions 138 passing through the temporary locking protrusions 160 are insertable. The temporary locking claw portions 138 extend in the axial direction.

As illustrated in FIG. 22, the base-portion body 154 has a non-circular shape along the outer shape of the second plunger 112 in a cross section perpendicular to the axial direction. The inner surface of the base-portion body 154 constitutes the second guide portion 164. The second guide portion 164 is engaged with the second guided portion 144 which is the inner surface of the second plunger 112, prevents rotation of the second plunger 112 with respect to the base portion 114, and guides axial movement of the second plunger 112.

As illustrated in FIG. 23, the support mechanism 116 includes a support member 166 arranged in the first plunger main body 122 so as to be non-rotatable relative to the first plunger main body 122 and movable in the axial direction relative to the first plunger main body 122, a third nut member 168 held by the support member 166, and an urging member 170 that elastically urges the support member 166 in the proximal direction. The support member 166 includes a pair of support arms 167 provided close to (or in contact with) the inner surface of the first plunger main body 122. As described later, the support arms 167 are capable of supporting the engagement elastic pieces 122a from inside.

The third nut member 168 is held so as to be non-rotatable with respect to the support member 166. A third female thread portion 168a is formed on the inner peripheral portion of the third nut member 168. In the initial state of the plunger assembly 14B, the third female thread portion 168a is threadedly engaged with the male thread portion 62 of the feed screw 108.

The urging member 170 is a coil spring arranged between the gasket pressing portion 124 of the first plunger 110 and the support member 166. The distal end of the urging member 170 is held in abutment against the distal-end wall portion of the insertion portion 124a of the gasket pressing portion 124. The proximal end of the urging member 170 is held in abutment against the support member 166. The central cylindrical portion 124c of the gasket pressing portion 124 is inserted into the urging member 170.

Next, the operation when the plunger assembly 14B is employed in the drug solution dosage device 10 will be described.

Figure 24:
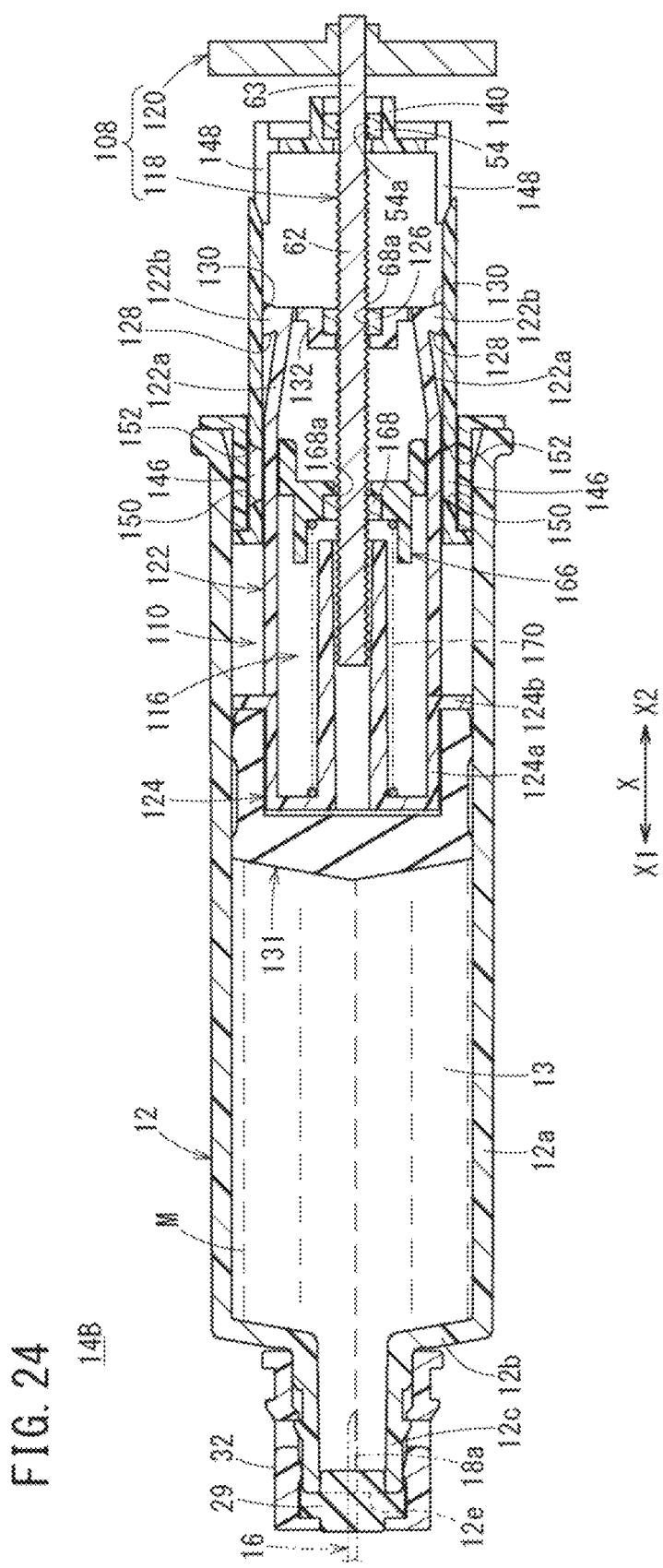
FIG. 24 is a first view illustrating an operation of the plunger assembly according to another embodiment.

When the feed screw 108 rotates by the drive mechanism 24 (FIG. 2) from the initial state illustrated in FIG. 23, the first plunger 110 threadedly engaged with the male thread portion 62 of the feed screw 108 moves forward as illustrated in FIG. 24. At this time, since the first guided portion 127 (outer surface of the first plunger main body 122) is guided by the first guide portion 142 (inner surface of the second plunger 112) (FIG. 22), the first plunger 110 moves forward (in a distal direction) with its rotation restricted. Since the third nut member 168 is threadedly engaged with the male thread portion 62, with the rotation of the feed screw 108, the support member 166 moves forward together with the first plunger 110.

On the other hand, since the temporary locking claw portions 138 of the second plunger 112 are inserted into the temporary locking protrusions 160 of the base portion 114 (FIG. 21), and the male thread portion 62 of the feed screw 108 is not threadedly engaged with the nut member 54 (the extending portion 63 of the feed screw 108 is inserted into the nut member 54), the second plunger 112 does not move forward even when the feed screw 108 rotates. Further, as illustrated in FIG. 24, when the first plunger 110 is to move forward, the engagement claw portions 122b of the first plunger 110 are disengaged from the proximal-end concave portions 148 of the second plunger 112 by a hinge function (elastic deformation function) of the engagement elastic pieces 122a and is drawn into the second plunger 112.

Figure 25:
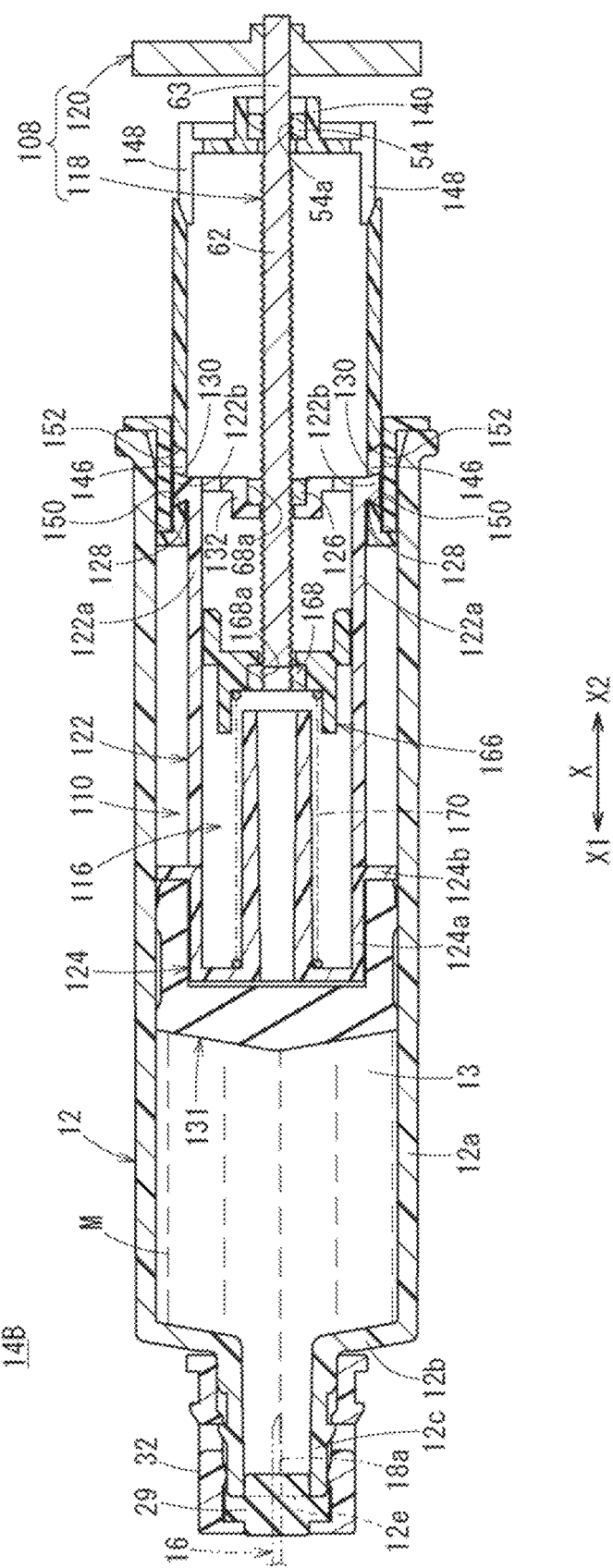
FIG. 25 is a second view illustrating the operation of the plunger assembly according to another embodiment.

As illustrated in FIG. 25, when the first plunger 110 and the support member 166 further move forward with the rotation of the feed screw 108, the third nut member 168 held by the support member 166 is disengaged from the male thread portion 62 of the feed screw 108. Therefore, after that, the third nut member 168 and the support member 166 do not move forward due to the rotation of the feed screw 108. Since the support member 166 is urged in the proximal direction by the urging member 170, the support member 166 is pressed against the distal end of the feed screw 108.

Further, with the forward movement of the first plunger 110, the engagement elastic pieces 122a of the first plunger 110 are displaced outward by its elastic restoring force, and the engagement claw portions 122b enter the distal-end concave portions 146 of the second plunger 112, so that the first engagement portions 128 (distal end surfaces of the engagement claw portions 122b) of the first plunger 110 are engaged with the second engagement portions 150 (distal end surfaces of the distal-end concave portions 146) of the second plunger 112.

Figure 26:
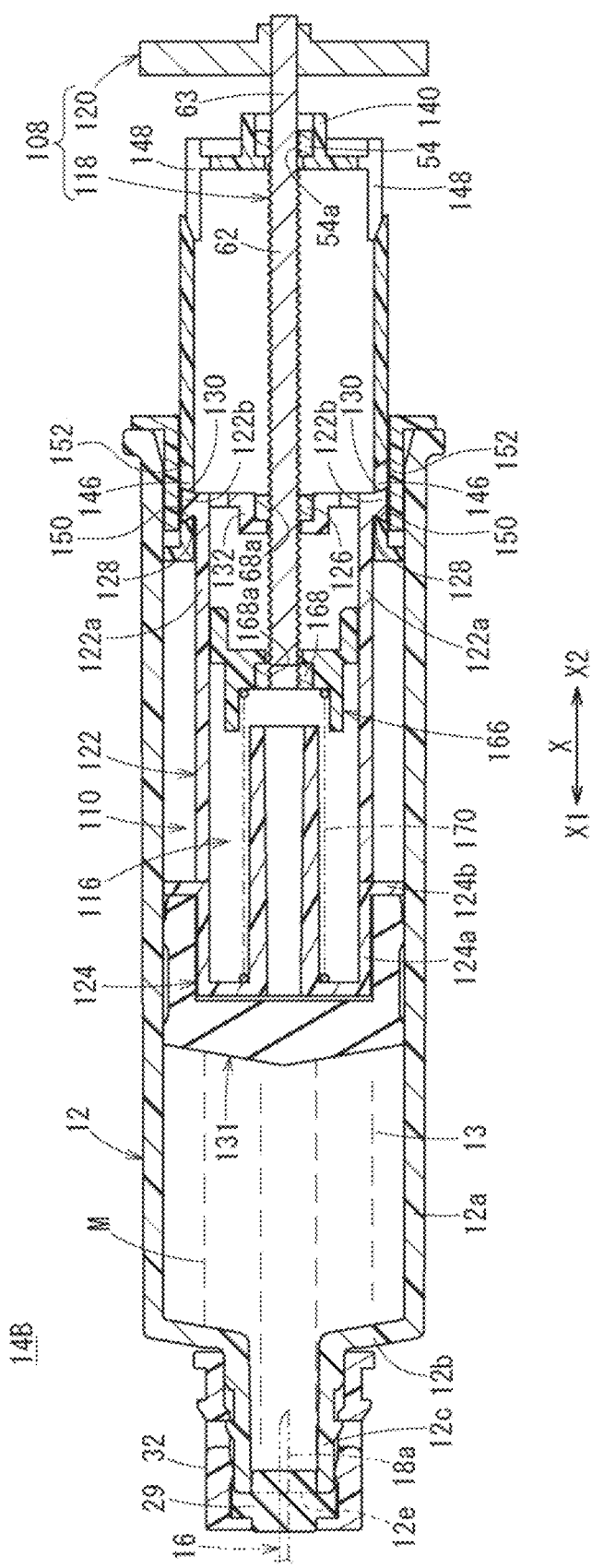
FIG. 26 is a third view illustrating the operation of the plunger assembly according to another embodiment.

Accordingly, as illustrated in FIG. 26, when the first plunger 110 moves forward with the first engagement portions 128 of the first plunger 110 and the second engagement portions 150 of the second plunger 112 engaged with each other, the first plunger 110 causes the second plunger 112 to move forward. That is, with the rotation of the feed screw 108, the first plunger 110 moves forward while pulling the second plunger 112. At this time, the temporary locking claw portions 138 (FIG. 21) of the second plunger 112 climb over the temporary locking protrusions 160 (FIG. 21) of the base portion 114, and enter the groove portions 162 (FIG. 21) provided on the inner surface of the base portion 114.

With the forward movement of the first plunger 110, the support member 166 urged in the proximal direction by the urging member 170 is displaced in the proximal direction relative to the first plunger 110 (the position of the support member 166 is not changed from the time when the thread engagement between the third nut member 168 and the male thread portion 62 is released). With the forward movement of the second plunger 112, the proximal end of the male thread portion 62 comes into contact with the distal end of the second female thread portion 54a of the nut member 54.

Figure 27:
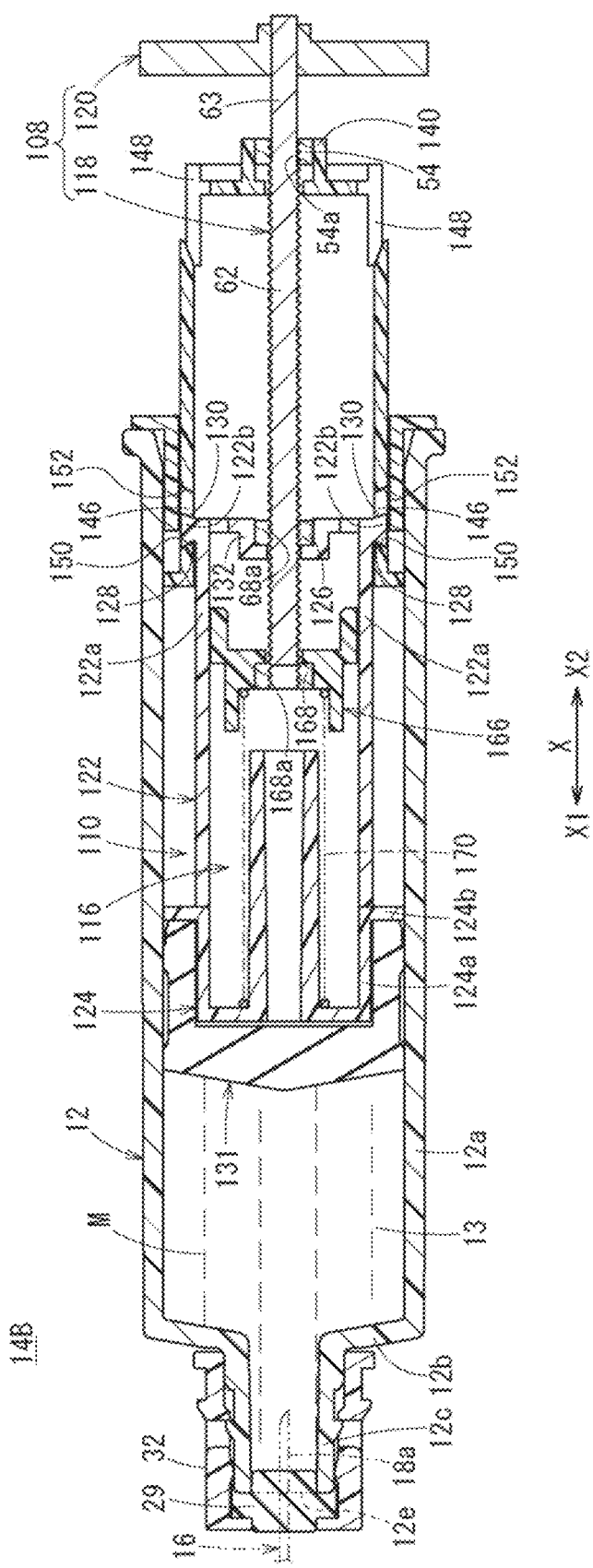
FIG. 27 is a fourth view illustrating the operation of the plunger assembly according to another embodiment.

As illustrated in FIG. 27, with the forward movement of the second plunger 112, the male thread portion 62 of the feed screw 108 is threadedly engaged with the second nut member 54 arranged on the second plunger 112. Specifically, even if the second nut member 54 fails to be threadedly engaged with the male thread portion 62 several times (for example, once or twice), with the forward movement of the second plunger 112, the second nut member 54 moves in the axial direction relative to the second plunger 112, thread engagement between the second nut member 54 and the male thread portion 62 is achieved. When the meshing between the male thread portion 62 and the second female thread portion 54a is started, a double screw state is started, in which the male thread portion 62 of the feed screw 108 is threadedly engaged with both the first female thread portion 68a and the second female thread portion 54a.

Then, with the rotation of the feed screw 108, the first plunger 110 and the second plunger 112 move forward in the double screw state. At this time, when the distal end surface of the nut member 54 is separated from the distal-end pedestal portion 89, the nut member 54 does not cause the second plunger 112 to move forward, but by the engagement between the first engagement portions 128 and the second engagement portions 150, the first plunger 110 causes the second plunger 112 to move forward.

Figure 28:
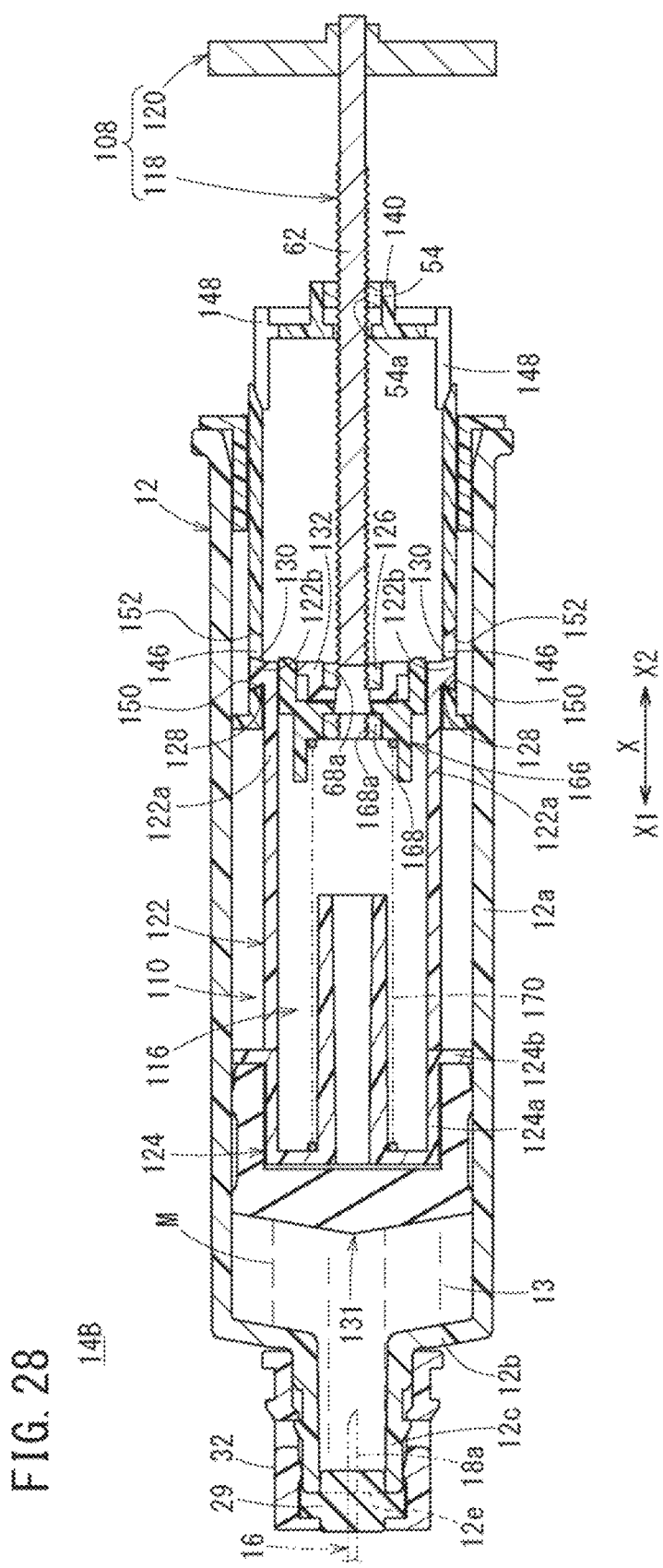
FIG. 28 is a fifth view illustrating the operation of the plunger assembly according to another embodiment.

When the first plunger 110 and the second plunger 112 further move forward with the rotation of the feed screw 108, as illustrated in FIG. 28, the first nut member 126 (first female thread portion 68a) of the first plunger 110 comes off the male thread portion 62 of the feed screw 108 (the thread engagement of the female thread portion 68a is released). With the forward movement of the first plunger 110, the support member 166 is displaced relative to the first plunger 110 until reaching a position where the nut accommodating portion 140 of the first plunger 110 comes into abutment against the support member 166. At this time, the support arms 167 of the support member 166 are located inside the engagement elastic pieces 122a.

Figure 29:
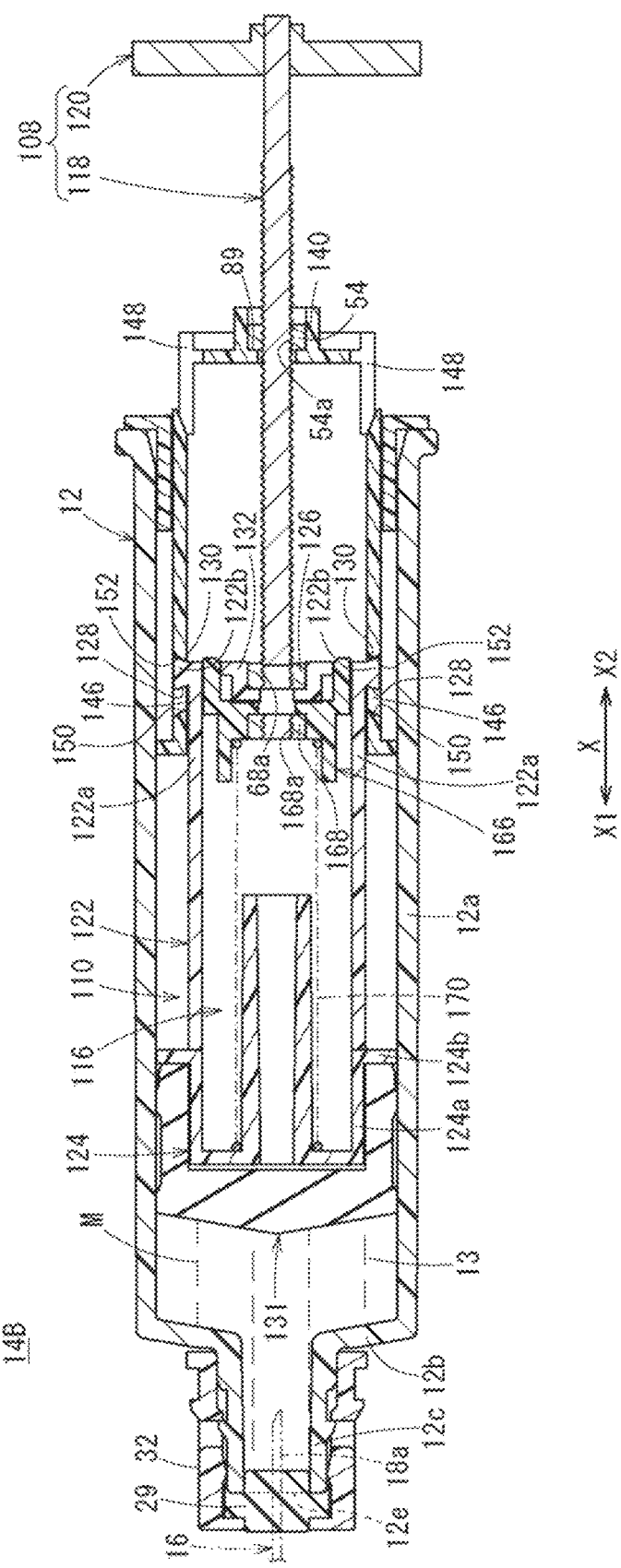
FIG. 29 is a sixth view illustrating the operation of the plunger assembly according to another embodiment.

When the thread engagement between the first plunger 110 and the feed screw 108 is released, as illustrated in FIG. 29, the second nut member 54 threadedly engaged with the feed screw 108 causes the second plunger 112 to move forward, and the second plunger 112 moving forward causes the first plunger 110 to move forward. Specifically, when the thread engagement between the first plunger 110 and the feed screw 108 is released, the second nut member 54 moves forward with the rotation of the feed screw 108, and comes into abutment against the distal-end pedestal portion 89 of the second plunger 112. Therefore, when the nut member 54 moving forward presses the distal-end pedestal portion 89 in the distal direction, the second plunger 112 starts to move forward.

Figure 30:
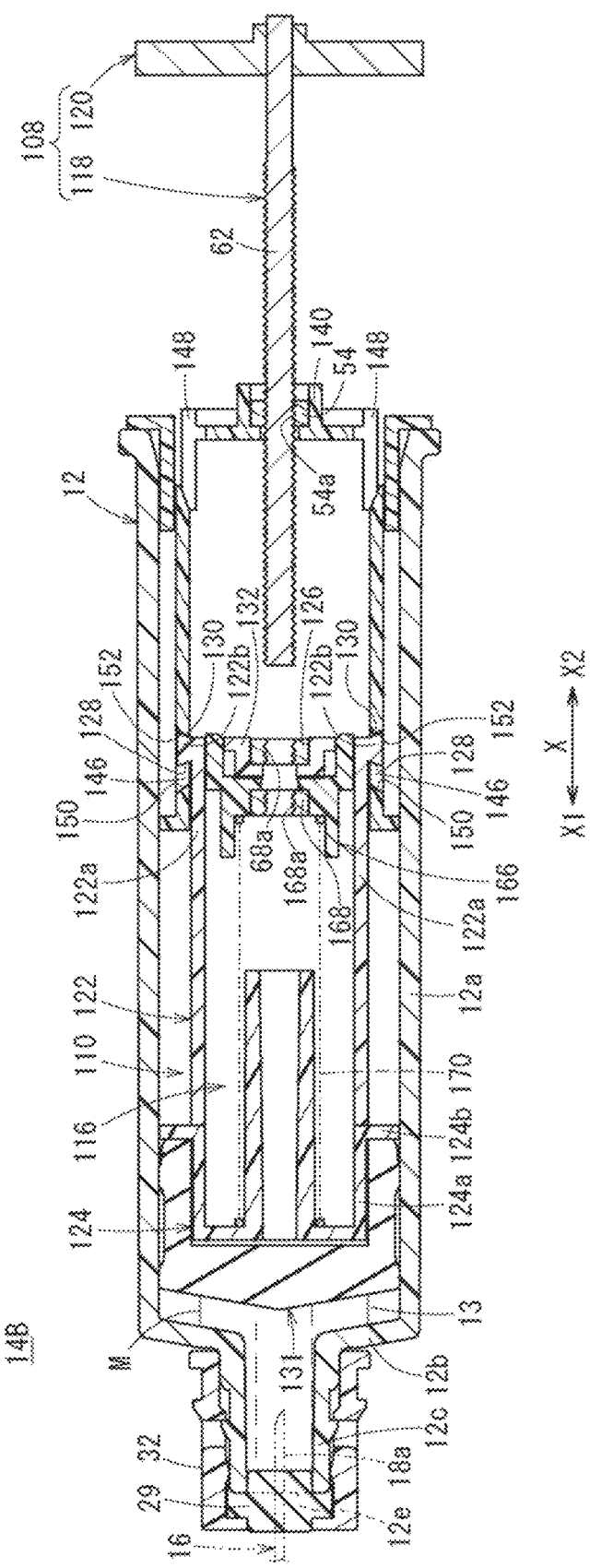
FIG. 30 is a seventh view illustrating the operation of the plunger assembly according to another embodiment.

At this time, since the first plunger 110, which has been released from the thread engagement with the feed screw 108, is stopped, with the forward movement of the second plunger 112, the second abutment portion 152 of the second plunger 112 comes into abutment against the first abutment portion 130 of the first plunger 110. Accordingly, as illustrated in FIG. 30, the second abutment portion 152 of the second plunger 112 moving forward presses the first abutment portion 130 in the distal direction, whereby the first plunger 110 starts to move forward again.

Accordingly, the first plunger 110 and the second plunger 112 move forward in a state where only the second nut member 54 is threadedly engaged with the feed screw 108, and liquid is fed. When the first plunger 110 moves forward, the support arms 167 of the support member 166 support the engagement elastic pieces 122a of the first plunger 110 from inside, so that the engagement claw portions 122b provided on the engagement elastic pieces 122a are prevented from being disengaged from the distal-end concave portions 146.

Figure 31:
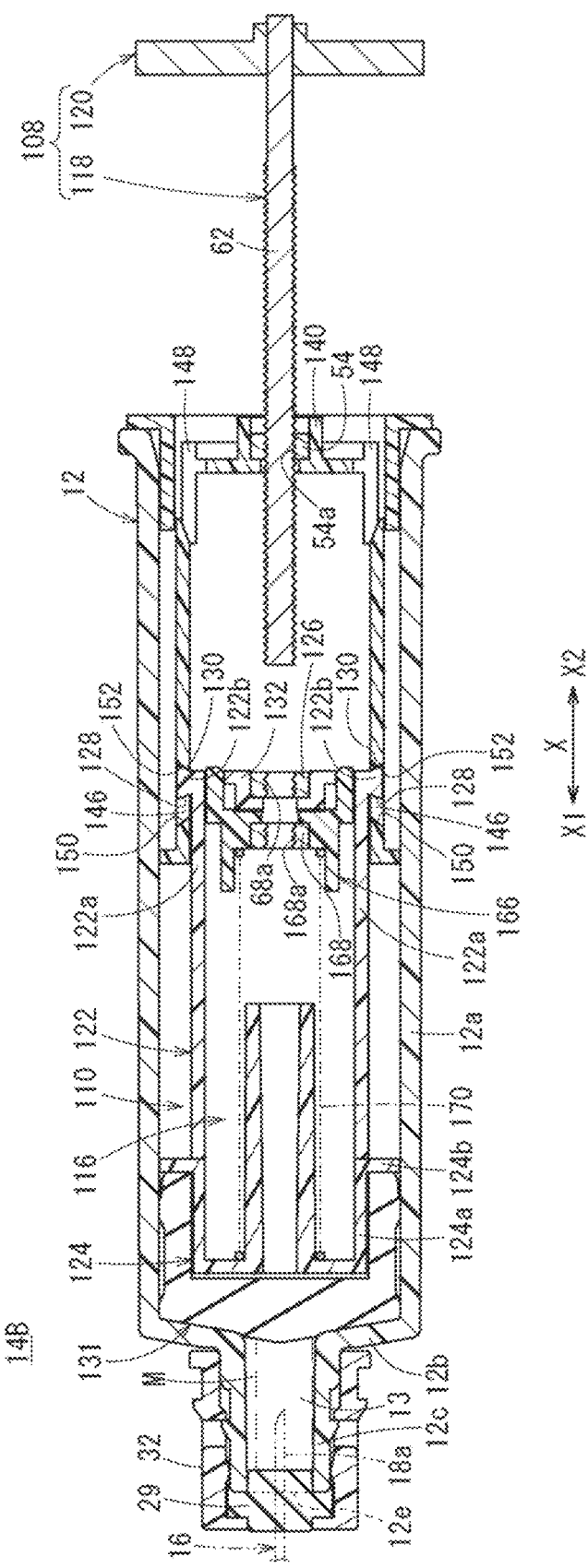
FIG. 31 is an eighth view illustrating the operation of the plunger assembly according to another embodiment.

Then, as illustrated in FIG. 31, when the first plunger 110 and the second plunger 112 move forward to a position where the gasket 131 comes into abutment against the shoulder portion 12b of the drug solution container 12, the rotation of the feed screw 108 stops, and the liquid feed is completed.

In the plunger assembly 14B, the same effects as those of the plunger assembly 14A can be obtained for components similar to those of the plunger assembly 14A.

The detailed description above describes embodiments of a plunger assembly, a drug solution dosage device, and a driving method of the plunger assembly. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A plunger assembly that is extendable in an axial direction and having a gasket slidably arranged inside a drug solution container to feed a drug solution from the drug solution container, the plunger assembly comprising:
   a feed screw including a rod portion, the rod portion including a male thread portion having a male thread formed on the rod portion, and an extending portion extending from a proximal end of the male thread portion in a proximal direction and not having the male thread formed on the extending portion;
   a first plunger including a gasket pressing portion, a first guided portion, a first engagement portion, and a first abutment portion, the gasket pressing portion configured to press the gasket, a first female thread portion threadedly engaged with the male thread portion of the feed screw at least in an initial state before the plunger assembly starts an extension operation;
   a second plunger including a first guide portion, a second guided portion, a second engagement portion, a second abutment portion, and a nut accommodating portion;
   a nut member having a second female thread portion formed on an inner periphery of the nut member, and into which the feed screw is inserted;
   a base portion having a second guide portion, the first guide portion of the second plunger is configured to engage with the first guided portion of the first plunger, to prevent rotation of the first plunger with respect to the second plunger, and to guide movement of the first plunger in the axial direction;
   the second guide portion of the base portion is configured to engage with the second guided portion, and to prevent rotation of the second plunger with respect to the base portion, and to guide movement of the second plunger in the axial direction;
   the nut accommodating portion configured to accommodate the nut member so that the nut member is non-rotatable and movable in the axial direction, and wherein the extending portion of the feed screw is inserted into the nut member in the initial state;
   wherein, when the first plunger moves forward by a predetermined length with rotation of the feed screw, the first engagement portion of the first plunger comes into abutment against the second engagement portion of the second plunger, and the first plunger causes the second plunger to move forward;

wherein, with the forward movement of the second plunger, the nut member moves forward, and the second female thread portion is threadedly engaged with the male thread portion of the feed screw; and wherein, after the thread engagement between the second female thread portion and the male thread portion is started, the second abutment portion of the second plunger comes into abutment against the first abutment portion of the first plunger, and the second plunger moving forward causes the first plunger to move forward.

2. The plunger assembly according to claim 1, further comprising:
a nut urging member configured to urge the nut member in a distal direction;
the nut accommodating portion of the second plunger includes a distal-end pedestal portion and a proximal-end pedestal portion; and
wherein, in the initial state, a distal end surface of the nut member is held in abutment against the distal-end pedestal portion, a distal end of the nut urging member is held in abutment against a proximal end surface of the nut member, and a proximal end of the nut urging member is held in abutment against the proximal-end pedestal portion.

3. The plunger assembly according to claim 1, wherein an inner peripheral surface of the nut accommodating portion includes a plurality of ribs extending along the axial direction and arranged at intervals in a circumferential direction, and wherein the plurality of ribs are held in abutment against an outer peripheral surface of the nut member.

4. The plunger assembly according to claim 1, wherein a distal end of the first plunger includes a flange portion configured to be held in abutment against an inner peripheral surface of the drug solution container.

5. The plunger assembly according to claim 1, wherein the second plunger includes:
a plunger main-body portion including the nut accommodating portion, the first guide portion, the second guided portion, and the second abutment portion; and
a cap member configured to be fixed to the plunger main-body portion and including the second engagement portion.

6. The plunger assembly according to claim 5, wherein the cap member includes a distal-end outer peripheral portion configured to be held in abutment against an inner peripheral surface of the drug solution container.

7. The plunger assembly according to claim 1, wherein the first guide portion of the second plunger includes an axial guide that extends along the axial direction and guides the first guided portion of the first plunger in the axial direction, and a rotation guide that is continuous with a distal end of the axial guide and extends in a circumferential direction to guide the first guided portion in the circumferential direction.

8. The plunger assembly according to claim 7,
wherein the rotation guide includes a first end portion continuous with the axial guide, and a second end portion different from the first end portion;
wherein the first guide portion of the second plunger includes a lock portion that is continuous with the second end portion of the rotation guide; and wherein the lock portion extends from the second end portion in the proximal direction with a length shorter than the axial guide, and is configured to lock the first guided portion of the first plunger.

9. The plunger assembly according to claim 1, wherein,
the second plunger includes a temporary locking elastic piece including a temporary locking claw portion provided at an end portion of the second plunger; and
the base portion includes a temporary locking concave portion into which the temporary locking claw portion is disengageably inserted.

10. The plunger assembly according to claim 9, wherein the first plunger includes a support protrusion that supports the temporary locking claw portion from inside of the first plunger.

11. A drug solution dosage device comprising:
the plunger assembly according to claim 1;
a drive mechanism configured to rotate the feed screw;
the drug solution container including a body portion filled with the drug solution;
the gasket; and
a casing configured to accommodate the drug solution container.

12. The drug solution dosage device according to claim 11,
wherein the drive mechanism includes a motor and a drive gear attached to the motor; and
wherein the feed screw includes a driven gear coupled to the rod portion and driven by the drive gear.

13. The drug solution dosage device according to claim 11,
wherein the casing including a first opening into which the drug solution container is inserted;
the drug solution container having a distal end portion protruding from the casing through the first opening; and
wherein a ring-shaped waterproof packing is arranged between the distal end portion of the drug solution container and the casing.

14. The drug solution dosage device according to claim 13, wherein the casing includes:
a casing main-body portion including an accommodating portion that accommodates the drug solution container and a second opening provided in the accommodating portion;
a lid that seals the second opening; and
an annular waterproof member attached to a rim of the second opening and in close contact with the lid.

15. The drug solution dosage device according to claim 14, further comprising:
a chassis structure in which the drug solution container, the drive mechanism, and the plunger assembly are fixed at predetermined positions, respectively;
wherein the chassis structure is arranged in the casing; and
wherein the second opening is larger than the chassis structure.

16. The drug solution dosage device according to claim 11,
wherein the first plunger is rotatable by a predetermined angle with respect to the second plunger with rotation of the feed screw at a distal end of the first guide portion of the second plunger;
wherein the gasket includes:
a gasket main body made of a first material having elasticity; and an abutment member made of a second material harder than the first material and mounted to a proximal end of the gasket main body, wherein the abutment member includes a pressed portion pressed by the gasket pressing portion, and wherein the gasket pressing portion is made of a material harder than the first material.

17. The drug solution dosage device according to claim 16, wherein
the abutment member includes an insertion portion inserted into the gasket main body, and a proximal-end flange portion provided at a proximal end of the insertion portion;
the proximal-end flange portion includes the pressed portion on a proximal end surface of the proximal-end flange portion; and
wherein the pressed portion is a plurality of convex portions provided intermittently on the proximal end surface and protruding from the proximal end surface in the proximal direction.

18. The drug solution dosage device according to claim 17, wherein each of the plurality of convex portions has a dome shape that bulges toward the proximal end of the gasket main body.

19. A driving method of the plunger assembly according to claim 1,
moving the first plunger forward along the axial direction with rotation of the feed screw;
engaging the first engagement portion of the first plunger with the second engagement portion of the second plunger, and the first plunger moving forward causes the second plunger to move forward;
moving the nut member in the proximal direction relative to the second plunger with the forward movement of the second plunger, and the movement of the nut member causing the nut member to be threadedly engaged with the male thread portion of the feed screw; and
moving the nut member threadedly engaged with the male thread portion forward with rotation of the feed screw to cause the second plunger to move forward, and the second plunger moving forward causes the first plunger to move forward.

20. The driving method of the plunger assembly according to claim 19, comprising:
urging the nut member in a distal direction by a nut urging member; and
wherein, after the nut member moves in the proximal direction relative to the second plunger against an urging force of the nut urging member, threadedly engaging the second female thread portion of the nut member with the male thread portion of the feed screw.

21. The driving method of the plunger assembly according to claim 19, comprising:
moving the first plunger restricted in rotation with respect to the feed screw to a vicinity of a distal end of the second plunger;
rotating the second plunger by a predetermined angle in accordance with rotation of the feed screw after the first plunger has moved to the vicinity of the distal end of the second plunger;
restricting the first plunger that has rotated by the predetermined angle in rotation again, and engaging the first engagement portion of the first plunger with the second engagement portion of the second plunger; and
engaging the first plunger in which the first engagement portion with the second engagement portion moving forward while pulling the second plunger.

22. The driving method of the plunger assembly according to claim 21, wherein, in a state where the male thread portion of the feed screw is threadedly engaged with both the first female thread portion and the second female thread portion, the driving method comprising:
rotating the feed screw and moving the first plunger and the second plunger forward;
wherein, after the second plunger moves forward by a predetermined length, disengaging the first female thread portion of the first plunger from the male thread portion; and
wherein the second plunger causes the first plunger to move forward in a state where the first female thread portion is disengaged from the male thread portion and the second female thread portion is threadedly engaged with the male thread portion.

* * * * *